US005710369A

United States Patent [19]
Fehr et al.

[11] Patent Number: 5,710,369
[45] Date of Patent: Jan. 20, 1998

[54] A16 SOYBEANS HAVING LOW LINOLENIC ACID CONTENT AND DESCENDENTS

[75] Inventors: Walter R. Fehr; Earl G. Hammond, both of Ames, Iowa

[73] Assignee: Iowa State University Research Foundation, Inc., Des Moines, Iowa

[21] Appl. No.: 656,017

[22] Filed: May 24, 1996

Related U.S. Application Data

[62] Division of Ser. No. 376,535, Jan. 20, 1995, Pat. No. 5,534,425, which is a continuation of Ser. No. 180,115, Jan. 12, 1994, abandoned, which is a continuation of Ser. No. 839,242, Feb. 20, 1992, abandoned, which is a continuation-in-part of Ser. No. 645,244, Jan. 24, 1991, abandoned, which is a continuation-in-part of Ser. No. 445,393, Dec. 5, 1989, abandoned, which is a continuation of Ser. No. 151,705, Feb. 3, 1988, abandoned.

[51] Int. Cl.$^6$ .............................. A01H 5/00; A01H 5/10
[52] U.S. Cl. ....................... 800/200; 800/230; 800/250; 800/DIG. 26; 800/DIG. 69; 47/58; 435/172.1
[58] Field of Search ........................... 800/200, 230, 800/250, DIG. 26, DIG. 69; 426/601; 47/58; 435/172.1

[56] References Cited

U.S. PATENT DOCUMENTS

| | | | |
|---|---|---|---|
| 4,581,847 | 4/1986 | Hibberd | 47/58 |
| 4,627,192 | 12/1986 | Fick | 47/58 |
| 4,948,811 | 8/1990 | Spinner et al. | 514/560 |

OTHER PUBLICATIONS

Hammond et al. Crop Sci. 23: 192, Registration of A5 Germplasm Line of Soybean, 1983.
"Improving the Fatty Acid Composition of Soybean Oil", E.G. Hammond et al., *JAOCS*, vol. 61, No. 11, (Nov. 1984), pp. 1713–1716.
"Genetic Alteration of Soybean Oil Composition by a Chemical Mutagen", J.R. Wilcox et al., *Journal of Am Oil Chemists Society*, vol. 61, No. 1, (Jan. 1984), pp. 97–100.
"Artificial Hybridization and Self–Pollination", Walter R. Fehr, *American Society of Agronomy–Crop Science Society of America*, (1980).
"Induction of Genetic Variation for Oil Properties and Agronomic Characeristics of Soybean", G.D. Brossman et al., *Crop Science*, vol. 24, Jul.–Aug. 1984, pp. 783–787.
"Resource Allocation in Breeding for Fatty Acid Composition of Soybean Oil", S.E. Hawkins et al., *Crop Science*, vol. 23, Sep.–Oct. 1983, pp. 900–904.
"Inheritance of Low Linolenic Acid Content of Seed Oil of a Mutant in Glycine max", J.R. Wilcox et al., *Theoretical and Applied Genetics*, (1985), vol. 71, pp. 74–78.
"Progress in Breeding for Low–Linolenic Acid Soybean Oil", Chapter 9, *Biotechnology for the Oils and Fats Industry*, by E.G. Hammond and Walter R. Fehr, (1980) Journal Paper No. J–10702, Project No. 2493, pp. 89–96. Edited by C. Ratledge, P. Dawson and J. Rattray, 1984, American Oil Chemists' Society.

"Oil Quality Improvement in Soybeans–Glycine max (L.) Merr.", *Sonderdruck aus fette*, by E.G. Hammond and Walter R. Fehr, Seifen, Anstrichmittel 77, pp. 97–101 (1975).
"Registration of A5 Germplasm Line of Soybean", E.G. Hammond et al., *Crop Science*, vol. 23, Jan.–Feb. 1983, p. 192.
"Registration of C1640 Soybean Germplasm", J.R. Wilcox et al., *Crop Science*, vol. 26, Jan.–Feb. 1986, pp. 209–210.
"Use of Tropical Environments in Breeding for Oil Composition of Soybean Genotypes Adapted to Temperate Climates", S.E. Hawkins et al., *Crop Science*, vol. 23, Sep.–Oct. 1983, pp. 897–899.
"Chapter XVII Processing of Edible Soybean Oil", J.W. Bodman et al., *Soybeans and Soybean Products*, (1951) Ed. Markely K.S. Interscience Publishers, N.Y., pp. 649, 702–709, 824, 825.
"Note on the Quality Constituents of Soybean (Glycine Max (L) Merril) Varieties", R.D. Tripathi et al., *Indian J. Agric. Res.*, 1975, 9(4), pp. 220–222.
"Comparison of Effects of Dietary Saturated, Monounsaturated, and Polyunsaturated Fatty Acids on Plasma Lipids and Lipoproteins in Man", Fred H. Mattson et al., *Journal of Lipid Research*, vol. 26, 1985, pp. 194–202.
"Cumulative Response to Various Recurrent Selection Schemes in Soybean: Oil Quality and Correlated Agronomic Traits", Brett F. Carver et al., *Crop Science*, vol. 26, Sep.–Oct. 1986.
"Chapter 7 Genetic Improvement in Soybean Oil", Keith J. Smith, *AOCS Monograph*, No. 11, pp. 71–75.
"Breeding Soybeans for Special Uses", O.G. Carter, *World Soybean Research Conference III Proceedings*, (1985), Westview Press, Inc., pp. 374–379.
"Breeding Soybeans for Improved Oil Quantity and Quality", J.R. Wilcox, *World Soybean Research Conference III Proceedings*, (1985), Westview Press, Inc., pp. 380–386 and pp. 386–391.
"The Linolenic Oils", A.E. Bailey, *Industrial Oils and Fats Products*, 1945 edition, p. 173.
"Relation Between the Fatty Acid Composition and the Iodine Number of Soybean Oil", C.R. Scholfield et al., *Oil & Soap*, Mar. 1944, pp. 87–89.
"Chapter 16: Oat Lipids", Earl G. Hammond, *Lipids in Cereal Technology*, 1983, pp. 331–352.
"Reviews: The Application of Genetic Engineering to Oilseed Crops", Vic. C. Knauf, *Tibtech*, Feb. 1987, vol. 5, Elsevier Science Publishers B.V., Amsterdam. pp. 40–47.

(List continued on next page.)

*Primary Examiner*—Elizabeth F. McElwain
*Attorney, Agent, or Firm*—Burns, Doane, Swecker & Mathis, L.L.P.

[57] ABSTRACT

A novel soybean seed and plant designated A16 having ATCC Accession No. and its descendents are provided. Such soybean exhibits an unusually low linolenic acid (C18:3) content of less than 2.5% by weight based upon the total fatty acid content in the endogenously formed vegetable oil.

3 Claims, No Drawings

OTHER PUBLICATIONS

"Notice to Plant Breeders and Seed Producers Relative to Release of Soybean Germplasm N85–2124, N85–2131, and N85–2176", Dr. R.J. Kuhr et al. (1987).

"Fatty Acid Composition of Margarines, Processed Fats, and Oils: A New Compilation of Data for Tables of Food Composition", John L. Weihrauch et al., *Food Technology*, vol. 31, Feb. 1977, pp. 80–85 and 91.

"Effect of Temperature of Soybean Seed Constituents: Oil, Protein, Moisture, Fatty Acids, Amino Acids and Sugars", R.B. Wolf et al., *American Oil Chemists' Society*, vol. 59, No. 5, May 1982, pp. 230–232.

"Effect of Genotype X Environment Interactions on Selection for Low Linolenic Acid Soybeans" M. M. Cramer et al., *Crop Science*, vol. 28, Mar.–Apr. 1984, pp. 327–330.

"Inheritance of Fatty Acid Composition in a Soybean Mutant With Low Linolenic Acid", G.L. Graef et al., *Crop Science*, vol. 28, (1988), pp. 55–58.

"Regulation of Linolenic Acid in Soybeans and Gene Transfer to High Yielding, High Protein Germplasm", *In Proceedings World Conference on Emerging Technology in Fat & Oil Industry*, AOCS Publisher, Baldwin (editor), pp. 386–391.

A16 SOYBEANS HAVING LOW LINOLENIC ACID CONTENT AND DESCENDENTS

This Application is a division of Ser. No. 08/376,535, filed Jan. 20, 1995, (now U.S. Pat. No. 5,534,425) which is a continuation of Ser. No. 08/180,115, filed Jan. 12, 1994 (now abandoned), which is a continuation of Ser. No. 07/839,242, filed Feb. 20, 1992 (now abandoned), which is a continuation-in-part of Ser. No. 07/645,244, filed Jan. 24, 1991 (now abandoned), which is a continuation-in-part of Ser. No. 07/445,393, filed Dec. 5, 1989 (now abandoned), which is a continuation of Ser. No. 07/151,705, filed Feb. 3, 1988 (now abandoned).

FIELD OF THE INVENTION

This invention relates to soybean seeds and to oils and other products made therefrom and, more particularly, to soybean seeds and oils, and methods for producing such seeds and oils, characterized by extremely low levels of linolenic acid.

BACKGROUND OF THE INVENTION

Soybean seeds represent perhaps the most significant oilseed in the world. Soybean oil makes up approximately 28% of the world supply of fats and oils, has been considered to be the major vegetable oil produced and consumed in the United States, and more than 90% of the soybean oil is used in food products (World Soybean Research Conference III Proceeding, Shibles, R. (Ed.) 1985).

Although soybean oil represents an important worldwide food source, flavor and stability problems reduce its utility in many applications. Soybean oil contains five different types of fatty acids. These five types of fatty acids are: palmitic acid (16:0), which averages about 11% of the total fatty acids; stearic acid (18:0), which averages about 4% of the total fatty acids; oleic acid (18:1), which averages about 20% of the total fatty acids; linoleic acid (18:2), which averages about 57% of the total fatty acids; and linolenic acid (18:3), which averages about 8% of the total fatty acids. The flavor stability problem of soybean oil has been attributed to the oxidation of its fatty acids, particularly to the oxidation of linolenic acid.

The unsaturated fatty acids in soybean oil are susceptible to oxidation; and the polyunsaturated fatty acids, linoleic and linolenic, oxidize more rapidly than oleic acid. The oxidized fatty acids apparently decompose to form volatile flavor compounds. It is not clear why linolenic acid contributes so significantly to the flavor and stability of oils; but, based upon experiments using blends of oils with different percentages of linolenic acid, all oils containing more than about 1% linolenic acid or so appear to share this property to some extent. For more than 35 years, the flavor and stability problems of soybean oil have been attributed to the high linolenic acid level of the soybean oil (Dutton et al., *J. Am. Oil Chem. Soc.*, 28:115, 1951).

To attempt to obviate the flavor and stability problems of soybean oil due to the linolenic acid content, various processes have been tried. Such processing includes (1) minimizing the ability of the fatty acids to undergo oxidation by adding metal chelating agents or packaging in the absence of oxygen, or (2) removal of the endogenous linolenic acid by selective hydrogenation. These approaches have not been entirely satisfactory. Such additional processing is expensive, time consuming, not completely effective and often generates undesirable by-products. Thus, while selective hydrogenation to reduce the linolenic acid content may improve oil stability, this also generates positional and geometric isomers of the unsaturated fatty acids that are not present in natural soybean oil.

The inability to solve the problem adequately, together with the undesirable aspects of the processing technology described herein, reduces the utility of soybeans, especially where such processing technology is either unavailable or is economically inappropriate or where consumer attitudes discourage the use of selective hydrogenation.

Perhaps because of the limitations of such processing technology and because of the worldwide significance of soybean oil as a food source, considerable effort has been expended over many years to attempt to understand the genetic mechanism which controls the linolenic acid level in soybeans. Indeed, studies on this subject date back to at least 1949. According to Howell et al., as many as five different genes may control the linolenic acid level in soybeans (*J. Am. Oil Chem. Soc.*, 26:126, 1949). Investigations into the biochemical mechanism suggest that linolenic acid results from successive desaturations of first oleic acid and second linoleic acid. Thus, genes controlling at least two different desaturase systems may be involved. So far, the genes which control the linolenic acid level of soybeans have not been fully identified; and the biochemical pathway has not been fully elucidated.

Even the mode of inheritance of linolenic acid in soybeans is unclear because various studies over the years have presented conflicting results. For example, early investigation suggested that the linolenic acid content in soybeans was maternally controlled. A later study suggested the mechanism of inheritance was even more complicated, being partially maternally and partially embryonically controlled (Wilson et al., *Regulation of Linolenic Acid in Soybeans and Gene Transfer of High Yielding, High Protein Germplasm*, R. A. Baldwin (Ed.), Proceedings of the World Conference on Emerging Technologies in the Fats and Oils Industry, Am. Oil Chem. Soc., Champaign, Ill., 1986). The Wilson et al. study thus reports that the genes which regulate oleic acid desaturation are controlled by the maternal parent, while the genes which control linoleic desaturation are governed by the embryonic genotype.

Complications also arise because it has been long recognized that the linolenic acid content of soybeans is highly dependent upon the environment in which the seeds are grown (Howell et al., *Agron. J.* 45:526, 1953). Such environmental factors are said to include temperature, photoperiod (viz.—day length), the geographical location and planting date.

In summary, despite the substantial effort over the years, the genetic mechanism controlling the linolenic acid content in soybeans is not all that well understood. Genetic research to provide soybeans characterized by reduced levels of linolenic acid is thus quite complex. There is little to guide efforts of this sort. Research is accordingly largely empirical.

Yet, despite the relative lack of understanding of the genetic mechanism which controls the level of linolenic acid content in soybeans, substantial work over the years has been carried out to attempt to isolate soybean lines having low levels of linolenic acid, as well as attempts to use genetic manipulation to develop a soybean line characterized by low levels of linolenic acid. The lowest level of linolenic acid in the oil of natural soybean germplasm accessions was found to be 4.2% (Kleinman and Cavins, *J. Am. Oil Chem. Soc.*, 59:305A, 1982).

Tripathi et al., *Indian J. Agric. Res.*, 1975, 9(4):220–222, *Note On The Quality Constituents Of Soybean (Glycine Max*

(L) Merrill) Varieties, did report, among other things, the fatty acid contents of what were stated to be 12 soybean varieties grown at the Oilseed Research Farm, Kalianpur, Kanpur, during kharif, 1970. While the linolenic acid contents reported vary from 0.0 to 5.3, such contents were calculated by the Scholfield and Bull formulae (Tripathi et al., referencing Bailey, 1945, *Industrial Oil and Fat Products*, Interscience Publishers, Inc., New York). In general, Scholfield and Bull's methodology predicted fatty acid composition from the iodine value. Their data were scattered about these linear predictions; and, for linolenic acid, a standard error of 1.5% was reported.

In the first place, the availability of the 12 soybean varieties referenced by Tripathi et al. is uncertain. Applicants have made repeated attempts to obtain samples of such varieties and have not been successful in securing all of them.

Secondly, and importantly, what has been determined on the basis of samples provided is that there is no correlation between the linolenic acid values reported by Tripathi et al. and those determined by gas chromatography. Gas chromatography is the current analytical standard used for fatty acid analysis. Set forth below, for all samples obtained, is a comparison of the linolenic acid values reported in Tripathi et al. with those obtained by gas-liquid chromatography (GLC):

| Variety | Tripathi et al. Values, % | GLC Values, % | |
|---|---|---|---|
| | | Seed From U.S.[1] | Seed from India[2] |
| Bragg | 4.5 | 7.6 | 5.8 |
| Type 49 | 4.9 | — | 5.9 |
| Lee | 3.7 | 6.7 | 4.0 |
| Improved Pelican | 2.4 | 7.2 | 7.0 |
| Punjab-1 | 0.4 | 6.1 | 5.6 |
| IC2716 | 1.0 | — | 4.4 |
| Type 33 | 5.3 | — | — |
| Type 64 | 0.0 | — | — |
| Type 1 | 1.4 | — | — |
| IC217 | 2.8 | — | 5.9 |
| IC222 | 4.1 | — | — |
| IC213 | 4.2 | — | — |

[1]Seed produced in United States and obtained from USDA, Soybean Production Research, Stoneville, Mississippi.
[2]Seed obtained from the National Bureau of Plant Genetic Resources, New Delhi, India.

In summary, based upon what applicants have found, there would be no basis for asserting that any of the varieties referenced by Tripathi et al. were varieties having low linolenic acid contents when such contents are determined by gas chromatography. Rather, these varieties appear to have rather typical linolenic acid contents, contents certainly above the minimum reported by Kleinman et al. for natural soybean germplasm accessions.

Hybridization work to reduce the linolenic acid of soybeans goes back as far as 1961. White et al. identified an $F_2$ plant obtained by hybridization with only 3.35% linolenic acid (White, Quackenbush and Probst, *Occurrence and Inheritance of Linolenic and Linoleic Acid in Soybean Seeds*, J. Am. Chem. Soc., vol. 38, pp. 113–117, 1961). However, this level was not maintained in succeeding generations.

Reported in 1975, the present applicants utilized recurrent selection to produce soybean strains having levels of linolenic acid of about 5.5% (Fette Seifen Anstrichm., 77:97–101, 1975). Wilson and Burton isolated two different lines, designated N78-2245 and PI123440. These lines were selected for their significant levels of oleic acid, linoleic acid and linolenic acid contents. From this experimentation, two genetic systems were discovered, one that primarily governs oleic acid desaturation and a second that acts genotypically upon linoleic desaturation. These two gene loci determine the low linolenic acid content (*Crop Science*, 21:788, 1981).

Wilcox et al. treated soybeans with ethyl methane sulfonate (EMS) to produce a mutant designated C1640 (*J. Am. Oil Chem. Soc.*, 61:97, 1984). The level of linolenic acid averaged 3.4%. It was stated that the linolenic acid trait could be transferred to other lines by backcrossing.

The present applicants were able to produce a mutant line A5 in 1983 which had an average of from about 2.9 to 4.1 percent linolenic acid depending upon the growth environment. This line was selected from the progeny of soybeans mutagenized with EMS (*Crop Science*, 23:192, 1983). More particularly, the mutant line A5 had an average linolenic acid percentage of 4.1% in one planting in Iowa and an average of 2.9% in two plantings in Puerto Rico. In a series of plantings involving five states, the average linolenic acid concentration for the A5 mutant was 3.8%. As will be discussed hereinafter, data generated in conjunction with the present invention revealed some A5 seeds having lower linolenic acid contents than the 2.9% previously noted. The seed of A5 (Reg. No. GP44) is publicly available and has been distributed by the Committee for Agricultural Development, Iowa State University, Ames, Iowa 50011, since 1983. A5 seed also is maintained by the Iowa Agriculture and Home Economics Experiment Station. Additionally, 2,500 seeds of A5 were deposited on Dec. 5, 1995 under the Budapest Treaty in the American Type Culture Collection (ATCC) at 12301 Parklawn Drive, Rockville, Md. 20852, U.S.A., and have been assigned ATCC Accession No. 97371.

The production of fatty acids in other plant systems, such as the sunflower, have been described, for example, in U.S. Pat. 4,627,192. In this case, a sunflower was disclosed which had a high oleic acid content and a low linoleic acid content.

A further interest for some applications would be the development of a soybean line characterized by not only low linolenic acid content, but also by a relatively high stearic acid content. More particularly, the production of plastic fats (e.g.—shortenings and margarines) with desirable physical properties can benefit from a soybean line having a relatively high stearic acid content. The A6 line (Reg. No. GP45) developed by applicants provides a soybean line having relatively high stearic acid contents (i.e. —28 to 30% or so), but such line has a relatively high linolenic acid content. A6 seed has been distributed by the Committee for Agricultural Development, Iowa State University, Ames, Iowa 50011, since 1983. A6 seed is maintained by the Iowa Agriculture and Home Economics Experiment Station.

Yet a further interest would be the development of a soybean line characterized by not only low linolenic acid content, but also by a moderately high palmitic acid content, i.e.—above 11%, more desirably in the range of 13 or 14 to 16% or so. Soybean lines having such moderately high palmitic acid contents may be desired for specific plastic fats; and, while current soybean lines can provide the desired palmitic acid contents, no existing soybean line or variety combines the desired palmitic acid content with a low linolenic acid content.

A still further interest would be the development of soybean lines characterized by not only low linolenic acid content, but also by a relatively high oleic acid content. Thus, for product applications where enhanced shelf-life or storage stability is required, it would be desirable to provide soybean lines characterized by a relatively high oleic acid and a relatively low linolenic acid content. Soybean lines having such characteristics would be highly desirable for commercial frying applications such as, for example, making potato chips or the like. It would even be more desirable for some applications to provide soybean lines having such characteristics that also have relatively low levels of saturated fatty acids.

An additional and related interest would be the development of soybean lines characterized by not only low linolenic acid content, but also by a relatively low palmitic acid content. More specifically, a major competitor of soybeans for the vegetable oil market is canola. Canola has been promoted as a healthier oil than soybean oil because of its relatively lower saturated fatty acid content. It would be a significant advance to be able to provide soybean oil that not only has the benefits associated with a relatively low linolenic acid content, but also which would have a palmitic acid content similar to that of canola.

Despite all of these prior efforts, there remains a current need for soybeans having a still further reduced level of linolenic acid. Indeed, it would be considered, from applicants' perspective, a breakthrough to be able to achieve soybean lines having linolenic acid contents, as determined by gas chromatography, of 2.5% or less, much less to be able to provide soybean lines having linolenic acid contents of 2.0% and less. A soybean line having relatively high stearic acid content and a linolenic acid content of 2.5% or less would be a further breakthrough. It would be yet a further breakthrough to combine, in a soybean line, a low linolenic acid content with a moderately high palmitic acid content. Still additional breakthroughs would thus involve, in a soybean line, the combination of a relatively low linolenic acid and a relatively high oleic acid content and also such a combination with a relatively low saturated fatty acid content. Yet another breakthrough would involve the combination, in a soybean line, of low linolenic and palmitic acid contents.

SUMMARY OF THE INVENTION

It has been discovered that soybean [Glycine max (L.) Merr.] varieties and lines characterized by low linolenic acid concentrations of less than about 2.5% of the total fatty acid present may be obtained by crossing selected mutant soybean strains. More particularly, out of literally hundreds of hybridization attempts which have been made over the years, applicants have discovered a limited number of parent mutant lines which, when crossed, yield a population of seeds characterized by extremely low linolenic acid concentrations. The particular parent mutant lines which have been found to result in the desired low linolenic acid trait will be described in the detailed description of the invention. Preferably, the present invention provides soybeans having a level of linolenic acid less than about 2.2% of the total fatty acid present and, in the most preferred embodiment, the level of linolenic acid is less than about 1.9% of the total fatty acid.

Progeny having the desired low linolenic acid concentration trait may then be crossed with other progeny (or with other desired soybean lines) to yield a population of soybean seeds which retain the desired low linolenic acid trait. Indeed, under the climatic conditions utilized, as will be discussed herein, the present invention provides soybean lines having a linolenic acid content as low as about 1.2% or so. Selective use of the more desired progeny, it is expected, should provide lines having linolenic acid contents even as low as about 1.0% or perhaps even somewhat less.

It has been also found that, among the progeny characterized by low linolenic acid content, some also share the moderately high palmitic acid content desired for some applications. Soybeans having an endogenous linolenic acid content of less than 2.5% by weight and a palmitic acid content of at least 11%, more desirably, 13 or 14% to up to 16% or more, are thus provided.

Still further, it has been discovered that, by crossing progeny having the desired low linolenic acid content with a parent having elevated levels of stearic acid, a soybean line can be provided which combines these characteristics. The stearic acid content is desirably at least 20%, more preferably at least 25%, and, even more preferably, at least 30% or more. Indeed, stearic acid contents of up to about 32% or so have been achieved. The linolenic acid content should be less than 3%, preferably less than about 2.5%, and even more preferably less than about 2.2%.

It has further been discovered that soybean lines having not only the desired low linolenic acid content, but also an oleic acid content of at least 60% can be obtained. Indeed, it has been discovered that such soybean lines can be obtained that also have relatively low palmitic acid and stearic acid contents.

Also, it has been discovered that soybean lines having not only the desired low linolenic acid content, but also a palmitic acid content less than about 6% can be obtained. Preferably, the palmitic acid content is less than about 5% and even more preferably, less than about 4.0%.

If the particular soybean line having the desired low linolenic acid trait lacks any characteristic desired, such line may be crossed with any cultivar having the characteristic desired. Suitable backcrossing techniques are known.

A preferred method for producing the low linolenic acid soybeans of the present invention involves planting early in the growing season. This has been found to make it more likely that the temperature during oil deposition, which temperature affects the linolenic acid content, will be more suitable to achieving particularly low linolenic acid contents.

DETAILED DESCRIPTION OF PREFERRED EMBODIMENTS

Regarding the terminology used herein, the terms "cultivar" and "variety" are used synonymously to refer to those soybean plants which share constant characteristics which separate them from other soybeans. The term varieties most often is used to refer to a commercial product. While possessing one or more distinctive traits, a variety like "Pella" or "Weber" is further characterized by a very small overall variation between individuals within that variety. A "line, strain or mutant" as distinguished from a variety most often denotes a group of plants used non-commercially, for example in plant research. A line, strain or mutant similarly displays very little overall variation between individuals sharing that designation. Unless otherwise indicated, all percentages refer to the percentage of the individual fatty acid under discussion compared to the total fatty acid composition in the soybean or oil on a weight basis. More accurately, as will be discussed hereinafter, in the gas chromatography methodology, what is reported, as is known, is the methyl ester of the fatty acid. Conversion to the fatty acid itself makes such an extremely minor difference that, for all intents and purposes, the reported values for the methyl ester can be taken as being the value for the free fatty acid itself.

It was originally perceived that the production of a soybean line having linolenic acid concentrations of less than 2.5% could be obtained by first crossing any moderately low linolenic soybean line (2.9–4.9%) with any high palmitic acid soybean line (greater than 11%). Then, a selection for those progeny producing the lowest levels of linolenic acid was carried out. However, upon further review of the substantial data which applicants have generated to date, it appears that this generic concept does not hold true.

Indeed, out of the literally hundreds of crosses which have been made, it has been discovered fortuitously that crossing rather select parent soybean lines provides a population of seeds with the desired low linolenic acid trait. More particularly, it has been found that crossing the mutant line A5 with any of the mutant lines, FA47437EMS, FA47451EMS, FA26315EMS, or FA26591EMS provides a population of soybean seeds exhibiting significantly reduced levels of linolenic acid in comparison to existing soybean lines. Seeds of each of these mutant lines have been deposited under the Budapest Treaty in the American Type Culture Collection (ATCC) at 12301 Parklawn Drive, Rockville, Md. 20852, U.S.A. More specifically, 625 seeds of FA47437EMS were deposited on Jan. 10, 1989 and have been assigned ATCC Accession No. 40537. 925 additional seeds of FA47437EMS were deposited on Dec. 19, 1995. 1,575 additional seeds of FA47437EMS were deposited on April 22, 1996. 2,500 seeds of FA47451EMS were deposited on Dec. 5, 1995 and have been assigned ATCC Accession No. 97372. 2,500 seeds of FA26315EMS were deposited on Dec. 5, 1995 and have been assigned ATCC Accession No. 97367. 550 seeds of FA26591EMS were deposited on Dec. 5, 1995 and have been assigned Accession No. 97369. 1,950 additional seeds of FA26591EMS were deposited on April 22, 1996. Thus, when planted under similar or the same conditions, the soybean lines of the present invention will have linolenic acid contents less than those of A5.

It has been further discovered that the crossing of one of the mutant lines previously identified, viz.—FA26591EMS, with line C1640 results in a population of seeds having the desired low linolenic acid trait. C1640 was developed at Purdue University and is a moderately low linolenic acid genotype. It is publicly available from James R. Wilcox, Department of Agronomy, Lilly Hall, Purdue University, Lafayette, Ind. 47907. 2,500 seeds of C1640 were deposited on Dec. 5, 1995 under the Budapest Treaty in the American Type Culture Collection (ATCC) at 12301 Parklawn Drive, Rockville, Md. 20852, U.S.A., and have been assigned Accession No. 97368. While the specific data obtained for the linolenic acid contents was not as low as that obtained when using the mutant line A5 as a parent, the linolenic acid content was substantially and significantly below that which had previously been obtained insofar as applicants are aware.

Still further, it has been discovered that the crossing of mutant line FA47451EMS with the mutant line A1937EMS-65 resulted in a population of seeds having the characteristic low linolenic acid level of the present invention. The mutant line A1937EMS-65 will be described in conjunction with the Examples. However, in general, this mutant line was obtained by treating the Asgrow variety A1937 with EMS. While the data obtained was less desirable than that for progeny resulting from the cross of lines FA26591EMS with the line C1640, the linolenic acid content is considered to be significantly less than that previously capable of being obtained.

Progeny exhibiting the desired low linolenic acid trait can be crossed with the parent lines previously identified herein to obtain a population of soybean seeds having particularly desirable linolenic acid contents. As an illustrative example, and as will be seen in the following Examples, the crossing of a parent line (e.g.—FA26591EMS) with progeny (viz.—selected from the crosses of the parent line A5 with the other mutant lines) provides a population of soybean seeds retaining the desirable low linolenic acid trait.

Still further, the crossing of selected progeny with other progeny likewise provides a population of soybean seeds having extremely low linolenic acid contents. In other words, the low linolenic acid trait of the soybean lines of the present invention is heritable. This can be seen from the following Examples.

Crossing to obtain the soybean lines of the present invention can be carried out by any desired hybrid formation technique. Standard hybridization techniques are, of course, well known and may be utilized. As an illustrative example, hybridization techniques are disclosed in Fehr, *Principles of Cultivar Development*, Vol. 1, Theory and Technique, Chapter 13, pp. 156–164, Macmillan Publishing Company, New York, 1987, which hybridization techniques are herein incorporated by reference.

Because the progeny resulting from the crosses identified herein which provide a population of seeds having the desired reduced level of linolenic acid may not themselves exhibit the seed yield and other agronomic characteristics desired for commercial production, the selection of low linolenic acid offspring by recurring backcrosses with a commercial variety can be conducted until a desirable commercial variety has been isolated. Backcrossing techniques are known, as disclosed in Fehr, *Principles of Cultivar Development*, Vol. 1, Theory and Technique, Chapter 28, pp. 360–376, the disclosure of which is herein incorporated by reference.

However, as one example, backcrossing using the desired $F_2$ seeds obtained by natural self-pollination of the $F_1$ plants could be carried out as follows:

(1) Plant $F_1$ seeds obtained by crossing a parent with the desired reduced linolenic acid trait to the desired commercial cultivar (recurrent parent). Sample $F_2$ seeds from $F_1$ plants are analyzed for fatty acid concentration, and seeds with the desired low linolenic acid content are planted for backcrossing.

(2) Cross-pollinate the desired commercial cultivar (recurrent parent) with the $F_2$ plant having the low linolenic acid content.

(3) Plant the $BC_1F_1$, seeds and obtain $BC_1F_2$ seeds by natural self-pollination. Sample $BC_1F_2$ seeds are analyzed for fatty acid concentration and those displaying the low linolenic acid trait are backcrossed to the recurrent parent.

(4) The backcross and selection procedure herein described (Step 3) can be repeated until lines with the desired low linolenic acid composition and agronomic performance are recovered. It is believed that four of these backcross cycles should serve to transfer the low linolenic acid trait to the desired cultivar (viz.—recurrent parent), although the number of such cycles can be fewer, or more, as is desired. The result is the production of a soybean line quite similar to the commercial cultivar except having the desired low linolenic acid content.

Any commercial cultivar (recurrent parent) desired may be employed for backcrossing. Factors such as, for example, seed yield, geographical area, and many others, as is known, will generally dictate the cultivar selected from the several hundred commercial cultivars available.

As will be seen in the Examples, progeny from the crosses described include soybean seeds wherein the linolenic acid composition is less than 2.5% of the total fatty acid composition, preferably less than about 2.2%, and more preferably less than about 1.9%. Surprisingly, soybean lines having as low as about 1.2% linolenic acid and even lower levels were obtained. Indeed, since there is no known requirement for linolenic acid in the soybean seed, it is theoretically possible that the methodology disclosed in the present invention may be utilized to yield soybean seeds, products and oil with down to zero linolenic acid. It can be expected that crosses utilizing the more desirable progeny should be capable of providing lines having linolenic acid contents down to about 1.0% or so.

According to one aspect of this invention, as will be seen from the following Examples, certain of the progeny not only possess the desired low linolenic acid trait, but also have the moderately high palmitic acid content preferred for some applications. Thus, as will be seen, soybeans according to the present invention can be provided with low linolenic acid content and a palmitic acid content of at least 11%, more desirably, at least 13 or 14%. Most of such applications desire, it is believed, soybeans having palmitic acid contents of 13 or 14% up to 16% or more.

In accordance with a further aspect of the present invention, soybean lines are provided having not only the desired low linolenic acid trait but also characterized by an extremely high stearic acid content. Such soybean lines may be obtained by crossing progeny having the desired low linolenic acid content with the A6 line. The resulting crosses can provide stearic acid contents even above 30%, up to about 32% or so. The particular stearic acid content will be determined by the needs of the specific application and that will generally be at least about 20% or so. While, in general, the lower the linolenic acid content the better, high stearic lines having linolenic acid contents of as much as 3.0% or so may be useful. More preferably, the linolenic acid contents of such lines are less than 2.5%, or even 2.2%.

Pursuant to yet another aspect of this invention, soybean lines are provided having not only the desired low linolenic acid trait but also characterized by an extremely high oleic acid content. Such soybean lines may be obtained crossing line AX4170-1-1-3 with line AX4174-1-8-9. Parent line AX4170-1-1-3 was obtained by crossing mutant line FA47437EMS with A5. Parent line AX4174-1-8-9 was obtained from the cross of A5 with mutant line FA26315EMS. Low linolenic soybean lines (viz.—less than about 3.0%, preferably less than 2.5 and even lower) may thus be provided with oleic acid contents in excess of about 60%, preferably in excess of about 64 or 65% or so. Indeed, progeny exhibiting the desired high oleic acid trait can be crossed with other progeny to provide a population of soybean seeds having an extremely high oleic acid content. It can be expected that crosses utilizing the more desirable progeny should be capable of providing lines having oleic acid contents of greater than about 70% or more, perhaps even up to about 75% or perhaps more.

In accordance with this specific aspect of the present invention, it has been discovered that soybean lines having not only the desired low linolenic acid content but also oleic acid contents above.70% may be obtained by crossing line A89–269077 with line AX7689-1-75. Parent line A89-269077 is an $F_2$ plant selection from the cross AX4692-123 with Harper 87. Harper 87 is a high yielding cultivar having about 8% linolenic acid. AX4692-123 is a 2% linolenic acid line selected from the cross of AX4170-1-14-4-6 with A84-284033. AX4170-1-14-4-6 is a 2% linolenic acid line selected from the cross of FA47437EMS with A5. A84-284033 is a high-yielding cultivar having about 8% linolenic acid. Parent line AX7689-1-75 was selected from the cross of A89-269041 with AX6002-1-4. A89-269041 is a 2% linolenic acid line whose parentage traces to the cross of FA47437EMS with A5. AX6002-1-4 is a 50% oleic and 2% linolenic acid line obtained from the cross of A87-192020 with AX4585-1-5-3. AX4585-1-5-3 is a line selected from the cross of FA26591EMS with AX4174. AX4174 being selected from the cross of FA26315EMS with A5. A87-192020 was selected from the cross of A83-214072-23-8 with NKS 23-03 A83-214072-23-8 being an $F_2$-derived line from the cross of Pella with A5.

Yet a further aspect of the present invention provides soybean lines having not only the desired low linolenic acid and high oleic acid contents, but also having an extremely low level of palmitic acid and/or stearic acid. Such soybean lines thus are characterized by an extremely low saturated fatty acid content.

Such soybean lines may be obtained by crossing AX4585-1-5-3 with AX5152-7. Parent line AX4585-1-5-3 was obtained by crossing mutant line FA26591EMS with AX4174-1-8-9. AX4174-1-8-9 was obtained from the cross of A5 with mutant line FA26315EMS. Parent line AX5152-7 was obtained from the cross of C1726 with A1937NMU-173.

These low linolenic, high oleic acid content soybean lines are further characterized by a palmitic acid content of no more than about 6.0% and/or a stearic acid content of no more than about 3.5%. It can be expected that crosses utilizing the more desired progeny should be capable of providing lines having palmitic acid contents of no more than 5.5% or 5.0% or perhaps even less and/or a stearic acid content of less than about 3.0% or somewhat less.

Further to this aspect of the present invention, it has been discovered that soybean lines having the desired low linolenic acid content but also low palmitic acid content may be obtained by crossing line A89-269077 with AX7345-2, an $F_1$ plant of the cross line AX5152-115 with A89-269077. Parent line A89-269077 is the 2.0% linolenic acid cultivar hereinbefore described, and parent line AX5152-115 is described in Example 2 of our copending application, Ser. No. 461,361 herein described, the disclosure regarding line AX5152-115 being herein incorporated by reference.

These low linolenic and palmitic acid content soybean lines are characterized by linolenic acid contents of less than about 3.0%, preferably less than about 2.5%, and even more preferably less than about 2.1%. The palmitic acid content is less than about 6.0%, preferably less than about 5.0%, and, more preferably, less than about 4.0%. It can be expected that crosses utilizing the more desired progeny should be capable of providing lines having linolenic acid contents of no more than about 1.0% and a palmitic acid content of no more than 3.0%, perhaps even no more than about 2.5%.

The fatty acid composition was determined by gas chromatography using the method as generally outlined in Graef et al. (*Crop Science*, 25:1076–1079, 1985). Thus, in general, the method comprises (1) crushing the seed sample, (2) putting the crushed sample into a test tube with a hexane solvent and extracting the oil into the hexane, (3) the fatty acids in the oil are converted to their methyl esters using sodium methoxide and methanol, (4) water is added to inactivate the sodium methoxide catalyst, and (5) the methyl esters, which float to the top of the water-methanol layer, are diluted with hexane and become the sample that is introduced into the column of the gas chromatography apparatus.

As may be appreciated, this general methodology may be employed and specific aspects changed to lessen the time needed as desired. For example, the stationary phase selected for the columns will dictate the temperature at which the sample can be introduced.

None of the specifics utilized, e.g.—capillary columns versus packed columns, are considered to affect to any appreciable extent the results obtained for an analysis. Rather, such specifics affect the time required for sample preparation and analysis.

The percentages of the fatty acids set forth herein, unless otherwise designated, thus are on a weight basis and refer to the percent of the methyl ester of linolenic or other fatty acid compared to the total methyl esters of the fatty acid composition in the sample being analyzed. This can also be taken as the weight percent of the free fatty acid itself because the difference between the linolenic acid content and that of its methyl ester as determined in the gas chromatography technique described herein is so minimal as may be ignored, as commonly done in this field.

The gas chromatographic techniques described herein are routinely used for analysis of the fatty acid composition of soybeans. The experimental error is considered to be within the range of from about 1 to 5% or so, depending upon the magnitude of the peak. For example, with a relatively large peak indicative of an oleic acid content of 50% or so, the experimental error may be as low as about 1% of the value, viz. −50% ±0.5%. At the other extreme, a small peak indicative of a linolenic acid content of 2.0% may have an experimental error of about 5% of the value, viz. −2.0% ±0.1%.

As may also be appreciated, the linolenic acid levels of the soybeans of the present invention set forth herein were obtained from soybeans grown in Iowa and Puerto Rico. Growth under conditions significantly cooler or warmer may result in a somewhat altered fatty acid composition. Specifically, early planting is preferred to facilitate development and maturity of the soybeans during the hot summer growing period thereby producing soybeans having the lowest level of linolenic acid, as illustrated in Example 18.

The early planting of the soybean seeds, under conditions such as planting about May 1 in a climate similar to Ames, Iowa, results, it is believed, in the lowest levels of linolenic acid. This may be the result of growing soybeans having an opportunity for development and maturation during the hot summer months. Such preferred development and maturation may be accomplished by planting soybeans early in the growing season with maturity reached during the warmest summer months. It is anticipated that these lower levels of linolenic acid in the soybeans of the present invention may be caused by a temperature-dependent, rate-limiting enzymatic step in the synthesis of linolenic acid. However, other aspects of plant physiology responding to the higher summer temperature may also be partially responsible for the low levels of linolenic acid. In Example 18, the A16 and A17 variety planted on May 1 had the lowest linolenic acid level found among plantings which occurred on May 1, May 15, May 30, and June 15. This is in contrast to the Century commercial soybean variety which exhibited its highest level of linolenic acid in the May 1 planting.

A preferred method for producing a substantially homogeneous crop of soybeans with linolenic acid content of less than 2.5%, and even more preferred, less than 2.2% of the total fatty acid composition, involves the planting of the soybeans under conditions to insure development and maturation under high temperatures. Such conditions may be accomplished by planting as early in the planting season as is physiologically acceptable to the growing region. This method for insuring high temperature development and maturation is accomplished by planting of soybean seeds as early in the growing season as is possible to avoid damaging environmental circumstances, such as frost or freezing weather. For each growing area, the production of low linolenic acid is favored, it is believed, by planting a soybean cultivar which reaches development and maturity during the hottest period of the growing season, while such a hot growing period in the northern hemisphere is best characterized by July and August, the months of May, June, September and October may also have sufficient or adequate temperatures. The method of producing soybeans having the low linolenic acid trait may also be accomplished by germinating and growing seeds in an environmental enclosure capable of simulating the conditions similar to Ames, Iowa, from planting about the first of May to development and maturation during July and August.

The preferred lower levels of linolenic acid may be achieved by utilizing early maturing varieties for the growing region. By crossing the low linolenic acid varieties of the present invention with such early maturing commercial varieties, the new varieties produced exhibit the most favorable low linolenic acid levels.

As is thus apparent, the planting and climatic conditions will yield soybeans having somewhat varying linolenic acid contents; however, under typical planting conditions, such as those experienced in Iowa and Puerto Rico, the linolenic acid content of the soybeans of the present invention will be below 2.5%, more typically below about 2.2%, and even more preferably below about 1.9%. Moreover, when planted under similar conditions, soybeans resulting from the present invention will have linolenic acid contents well below that resulting from any soybean line previously known.

More specifically, the linolenic acid content observed in some instances for "selfed" (i.e.—self-pollinated) A5 is below the levels noted in the 1983 plantings previously discussed. Indeed, in a few instances, it has been observed that seeds of selfed A5 had linolenic acid contents determined to be as low as 2.5% and down to about 2.4%, perhaps 2.3% or so. However, as is also evident from the following Examples, the soybean seeds of the present invention, when planted under the same or similar conditions as A5 seeds, uniformly yield soybean plants having endogenous linolenic acid contents less than that of the A5 plants.

Further, it is possible that planting the soybean seeds of the present invention under particularly adverse conditions could result in soybean plants having linolenic acid contents about 2.5%. Accordingly, as is implicit herein, the linolenic acid contents set forth herein, refer to what results from using more typical as opposed to extreme conditions. Again, the use of such extreme conditions will likewise increase even further the linolenic acid content of prior soybean lines, such as A5.

In similar fashion to that of the linolenic acid content, the palmitic, stearic and oleic acid contents of the soybean lines of the present invention were obtained from soybeans grown in Iowa and Puerto Rico. Growth under conditions significantly cooler or warmer may result in a somewhat altered fatty acid composition. However, the soybeans of the present invention will consistently exhibit the desired palmitic, stearic, and oleic acid contents in comparison to previously known soybeans when planted under the same or similar conditions.

Still further, as will be seen in the following Examples, the linolenic acid contents of a particular line may vary somewhat significantly from generation-to-generation. However, as will also be seen, the soybeans of the present invention exhibit linolenic acid contents consistently lower than any previously known soybeans when planted under the same or similar conditions.

Three soybean varieties have been deposited under the Budapest Treaty in the American Type Culture Collection (ATCC) at 12301 Parklawn Drive, Rockville, Md. 20852, U.S.A. Variety FA47437EMS has been assigned Accession No. 40537; varieties A16 (AX4170-1-1-2) and A17 (AX4170-1-15-2) have been respectively assigned Accession No. 40538 and Accession No. 40539. 625 seeds of FA47437EMS were deposited on Jan. 10, 1989, 925 additional seeds were deposited on Dec. 19, 1995, and 1,575 additional seeds were deposited on Apr. 22, 1996. 625 seeds of A16 were deposited on Jan. 10, 1989. An additional 1,875 seeds of A16 were deposited on Dec. 27, 1996. 625 seeds of A17 were deposited on Jan. 10, 1989, an additional 1,175 seeds were deposited on Dec. 19, 1995, and an additional 1,325 seeds were deposited on Apr. 22, 1996. Variety FA47437EMS was crossed with A5 as described in Example 6 to yield a variety of progeny including A16 and A17. A16 and A17 represent the preferred embodiments. Both have the desired low linolenic acid characteristics. The A16 variety has a more typical palmitic acid content, while the A17 variety has a somewhat elevated palmitic acid content.

The following Examples are illustrative, but not in limitation, of the present invention. The gas chromatography results obtained from the instrument itself are reported to two decimal points (i.e.—"0.00"). As reported herein, the fatty acid values are set forth to one decimal point. Values of 6 or more in the second decimal point were raised (e.g.— 2.29 is reported herein as 2.3), values of 4 or less are ignored (e.g.—2.24 is reported as 2.2), values of 5 are raised if the first decimal is odd (e.g.—2.15 is reported as 2.2) and ignored if even (e.g.—2.25 is reported as 2.2).

EXAMPLE 1

This Example describes the preparation of the mutant line FA47437EMS.

Mutant line FA47437EMS was obtained from ethyl methanesulfonate (EMS) treatment of the parent strain FA47437. On June 1, 2,500 seeds of each parent were soaked in 2.5 L distilled water in a 6 L flask for 9 hours at room temperature. The flask was aerated for the 9 hours of soaking. The water was drained from the flask, and 2.5 L of 0.1 molar phosphate buffer at pH 7 and 0.025 molar EMS were added. The seeds were soaked for 9 hours, the solution was drained and the seeds were rinsed twice with distilled water. Treated seeds were placed in containers to prevent drying and transported to the Agricultural Engineering and Agronomy Research Center near Ames, Iowa. The seeds were planted 2.5 cm deep in moist soil within 4 hours after the last rinse. The soil was watered regularly to keep it moist until seedling emergence.

The properties of the mutant seed and their progeny were evaluated through five generations.

A similar number of seeds was harvested from each of the $M_1$ (first mutant generation) plants in a population to obtain 2,000 $M_2$ seeds for each population. A random sample of 1,000 of the second generation $M_2$ seeds for each population was planted in November at the Iowa State University—University of Puerto Rico soybean nursery at Isabela, Puerto Rico. At least 2,000 $M_3$ seeds from each population were obtained by harvesting four seeds from each plant. In February, 1,000 $M_3$ seeds were planted in Puerto Rico. At least 2,000 $M_4$ seeds were obtained by harvesting four seeds from each plant. In June, 1,000 $M_4$ seeds were planted at Ames. Five hundred $M_4$ plants were harvested individually from each population, and a 10-seed sample from each plant was analyzed by gas-liquid chromatography to determine the fatty acid composition. $M_5$ progeny of the mutant plants were evaluated, and the results confirmed the unique fatty acid composition of the $M_4$ parent plants.

The mutant strain FA47437EMS will be utilized in making crosses using standard hybridization procedures to prepare soybeans having the low linolenic acid trait characteristic of the present invention.

EXAMPLE 2

A parent mutant line FA47451EMS was prepared using the same procedure as described in Example 1, except that FA47451 was used in place of FA47437.

EXAMPLE 3

A parent mutant line FA26315EMS was prepared using the same procedure as described in Example 1, except that FA26315 was used in place of FA47437.

EXAMPLE 4

A parent mutant line FA26591EMS was prepared using the same procedure as described in Example 1, except that FA26591 was used in place of FA47437.

EXAMPLE 5

A parent mutant line A1937EMS-65 was prepared using the same procedure as described in Example 1, except that Asgrow A1937 was used in place of FA47437. 2,500 seeds of a1937EMS-65 were deposited on Dec. 5, 1995 under the Budapest Treaty in the American Type Culture Collection (ATCC) at 12301 Parklawn Drive, Rockville, Md. 20852, U.S.A., and have been assigned Accession No. 97370.

EXAMPLE 6

This Example describes the crossing of parent A5 with the mutant line FA47437EMS prepared as described in Example 1 to obtain soybeans of the present invention. The hybrid $F_I$ seeds obtained from the cross were designated AX4170.

$F_1$ plants of the cross AX4170 were grown in the Iowa State University—University of Puerto Rico nursery at Isabela, Puerto Rico. $F_2$ seeds were obtained by natural self-pollination. Each $F_1$ plant was harvested individually, and the $F_2$ seeds of each were maintained as separate subpopulations of the cross.

One hundred $F_2$ seeds from the $F_1$ plant designated AX4170-1 were planted in the Iowa State University—University of Puerto Rico nursery at Isabela, Puerto Rico. $F_3$ seeds were obtained by natural self-pollination. Each $F_2$ plant was harvested individually.

A 10-seed sample from each $F_2$ plant was analyzed by gas-liquid chromatography at Iowa State University. An analysis of individual split seeds from the $F_2$ plants and parent lines was also made. Two $F_2$ plants designated AX4170-1-1 and AX4170-1-15 were selected with a linolenic acid percentage lower than that of either parent and lower than that previously described for soybeans.

The fatty acid composition of the soybeans of the present invention as well as that of the parent mutant lines is set forth in Table I, the values set forth being the mean of the split seeds rather than those of the 10-seed bulk sample since the split seed values are considered to be more representative:

TABLE I

| Seed Identification | Fatty Acid Composition | | | | |
|---|---|---|---|---|---|
|  | Palmitic Acid (16:0) | Stearic Acid (18:0) | Oleic Acid (18:1) | Linoleic Acid (18:2) | Linolenic Acid (18:3) |
| AX4170-1-1 | 13.8 | 3.2 | 42.0 | 39.2 | 1.9 |
| AX4170-1-15 | 17.0 | 2.8 | 28.3 | 49.6 | 2.4 |
| FA47437EMS | 16.8 | 3.8 | 32.2 | 42.4 | 4.7 |
| A5 | 9.1 | 2.8 | 58.4 | 27.0 | 2.8 |

$F_3$ seeds from the $F_2$ parent plants AX4170-1-1 and AX4170-1-15 were planted in Puerto Rico. Ten individual $F_3$ plants were harvested from each of these $F_2$ parent plants. The fatty acid composition of the $F_3$ plants AX4170-1-1-2 and AX4170-1-15-2 was determined and is set forth in Table II:

TABLE II

| Seed Identification | Fatty Acid Composition | | | | |
|---|---|---|---|---|---|
|  | Palmitic Acid (16:0) | Stearic Acid (18:0) | Oleic Acid (18:1) | Linoleic Acid (18:2) | Linolenic Acid (18:3) |
| AX4170-1-1-2 | 11.0 | 4.5 | 34.0 | 48.1 | 2.4 |
| AX4170-1-15-2 | 16.4 | 3.6 | 28.3 | 49.5 | 2.2 |
| FA47437EMS | 17.7 | 4.1 | 23.7 | 48.8 | 5.7 |
| A5 | 10.0 | 3.6 | 44.5 | 38.4 | 3.4 |

$F_4$ seeds from individual $F_3$ parent plants AX4170-1-1-2 and AX4170-1-15-2 were planted at the Agricultural Engineering and Agronomy Research Center. Individual $F_4$ plants were harvested from each $F_3$ parent plant. The fatty acid composition of the $F_4$ generation was determined and is set forth in Table III:

TABLE III

| Seed Identification | Fatty Acid Composition | | | | |
|---|---|---|---|---|---|
|  | Palmitic Acid (16:0) | Stearic Acid (18:0) | Oleic Acid (18:1) | Linoleic Acid (18:2) | Linolenic Acid (18:3) |
| AX4170-1-1-2 | 10.4 | 4.6 | 33.2 | 49.8 | 2.0 |
| AX4170-1-15-2 | 15.1 | 3.8 | 39.1 | 40.0 | 1.9 |
| A5 | 10.1 | 3.4 | 38.2 | 44.8 | 3.4 |

FA47437EMS was not grown in the test

Thus, as has been seen, the cross of the two mutant lines resulted in a population of soybeans having extremely low linolenic acid contents. It is considered that the $F_2$, $F_3$ and $F_4$ plant data confirm that stable genotypes were developed having the lowest linolenic acid percentages ever reported for soybeans insofar as applicants are aware.

EXAMPLE 7

This Example describes the crossing of parent line A5 with the mutant line FA47451EMS prepared as described in Example 2 to obtain soybean lines of the present invention. The hybrid $F_1$ seeds obtained from the cross were designated AX4172.

$F_1$ plants were grown as described in Example 6. $F_2$ seeds were obtained by natural self-pollination. Each $F_1$ plant was harvested individually, and the $F_2$ seeds of each were maintained as separate subpopulations of the cross.

One hundred $F_2$ seeds from the $F_1$ plant designated AX4172-1 were planted as described in Example 6. $F_3$ seeds were obtained by natural self-pollination. Each $F_2$ plant was harvested individually.

A 10-seed sample from each $F_2$ plant was analyzed by gas-liquid chromatography at Iowa State University. Two $F_2$ plants designated AX4172-1-24 and AX4172-1-35 were selected with a linolenic acid content being lower than that of either parent.

The fatty acid composition of the soybeans of the present invention as well as that of the parent mutant lines is set forth in Table IV:

TABLE IV

| Seed Identification | Fatty Acid Composition | | | | |
|---|---|---|---|---|---|
|  | Palmitic Acid (16:0) | Stearic Acid (18:0) | Oleic Acid (18:1) | Linoleic Acid (18:2) | Linolenic Acid (18:3) |
| AX4172-1-24 | 8.7 | 2.8 | 62.4 | 24.1 | 2.0 |
| AX4172-1-35 | 14.5 | 1.8 | 52.3 | 29.3 | 2.1 |
| FA47451EMS | 17.0 | 3.8 | 31.1 | 42.4 | 5.7 |
| A5 | 9.5 | 2.9 | 58.1 | 26.6 | 2.9 |

$F_3$ seeds from the $F_2$ parent plants AX4172-1-24 and AX4712-1-35 were planted in Puerto Rico. Ten individual $F_3$ plants were harvested from each of these $F_2$ parent plants. The fatty acid composition of the $F_3$ plants AX4172-1-24-3 and AX4172-1-35-8 was determined and is set forth in Table V:

TABLE V

| Seed Identification | Fatty Acid Composition | | | | |
|---|---|---|---|---|---|
|  | Palmitic Acid (16:0) | Stearic Acid (18:0) | Oleic Acid (18:1) | Linoleic Acid (18:2) | Linolenic Acid (18:3) |
| AX4172-1-24-3 | 9.6 | 4.3 | 39.7 | 43.1 | 3.3 |
| AX4172-1-35-8 | 16.8 | 3.3 | 30.5 | 46.0 | 3.3 |
| FA47451EMS | 16.4 | 4.2 | 21.2 | 50.5 | 7.7 |
| A5 | 9.1 | 3.5 | 52.0 | 32.0 | 3.4 |

$F_4$ seeds from the individual $F_3$ parent plants were planted at the Agricultural Engineering and Agronomy Research Center at Ames, Iowa. Individual plants were harvested from each $F_3$ parent plant. The fatty acid composition of the $F_4$ generation was determined and is set forth in Table VI:

TABLE VI

| Seed Identification | Fatty Acid Composition | | | | |
|---|---|---|---|---|---|
|  | Palmitic Acid (16:0) | Stearic Acid (18:0) | Oleic Acid (18:1) | Linoleic Acid (18:2) | Linolenic Acid (18:3) |
| AX4172-1-24-3 | 10.4 | 4.0 | 43.4 | 39.6 | 2.5 |
| AX4172-1-35-8 | 16.0 | 3.6 | 42.7 | 34.9 | 2.8 |
| FA47451EMS | 15.6 | 4.9 | 34.8 | 40.9 | 3.8 |
| A5 | 10.0 | 3.1 | 39.3 | 44.1 | 3.5 |

EXAMPLE 8

This Example describes the crossing of parent line A5 with the mutant line FA26315EMS prepared as described in Example 3. The hybrid $F_1$ seeds obtained from the cross were designated AX4174.

$F_1$ plants were grown as described in Example 6. $F_2$ seeds were obtained by natural self-pollination. Each $F_1$ plant was harvested individually, and the $F_2$ seeds of each were maintained as separate subpopulations of the cross.

One hundred $F_2$ seeds from the $F_1$ plant were planted as in Example 6. $F_3$ seeds were obtained by natural self-pollination. Each $F_2$ plant was harvested individually.

A 10-seed sample from each $F_2$ plant was analyzed by gas-liquid chromatography at Iowa State University. Two $F_2$ plants designated AX4174-2-6 and AX4174-5-8 were selected with a linolenic acid content being lower than that of either parent.

The fatty acid composition of the soybeans of the present invention as well as that of the parent mutant lines is set forth in Table VII:

TABLE VII

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4174-2-6 | 11.6 | 1.9 | 63.8 | 20.5 | 2.1 |
| AX4174-5-8 | 14.9 | 1.2 | 47.8 | 33.9 | 2.2 |
| FA26315EMS | 13.8 | 1.9 | 47.0 | 33.8 | 3.6 |
| A5 | 9.3 | 2.7 | 55.6 | 27.6 | 2.8 |

$F_3$ seeds from the $F_2$ parent plants AX4174-2-6 and AX4174-5-8 were planted in Puerto Rico. Ten individual $F_3$ plants were harvested from each of these $F_2$ parent plants. The fatty acid composition of the $F_3$ plants AX4174-2-6-4 and AX4174-5-8-4 was determined and is set forth in Table VIII:

TABLE VIII

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4174-2-6-4 | 10.0 | 3.7 | 36.4 | 46.9 | 3.0 |
| AX4174-5-8-4 | 16.1 | 3.6 | 32.4 | 44.6 | 3.2 |
| FA26315EMS | 16.0 | 5.5 | 31.2 | 42.2 | 5.0 |
| A5 | 10.0 | 3.1 | 39.3 | 44.1 | 3.5 |

EXAMPLE 9

This Example describes the crossing of the parent line A5 with the mutant line FA26591EMS prepared as described in Example 4 to obtain the soybean lines of the present invention. The hybrid $F_1$ seeds obtained from the cross were designated AX4416.

$F_1$ plants of the cross AX4416 were grown in the Iowa State University—University of Puerto Rico nursery at Isabela, Puerto Rico. $F_2$ seeds were obtained by natural self-pollination. Each $F_1$ plant was harvested individually, and the $F_2$ seeds of each were maintained as separate subpopulations of the cross.

A total of 200 $F_2$ seeds from the cross were planted in the Iowa State University—University of Puerto Rico nursery at Isabela, Puerto Rico. $F_3$ seeds were obtained by natural self-pollination. One hundred $F_2$ plants were harvested individually.

A 10-seed sample from each $F_2$ plant was analyzed by gas-liquid chromatography at Iowa State University. The $F_2$ plant designated AX4416-7-2 was selected with a linolenic acid percentage lower than that of either parent.

The fatty acid composition of the soybeans of the present invention as well as that of the parent mutant lines is set forth in Table IX:

TABLE IX

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4416-7-2 | 9.8 | 3.4 | 54.1 | 30.7 | 2.0 |
| FA26591EMS | 9.0 | 3.9 | 44.7 | 38.0 | 4.4 |
| A5 | 9.7 | 2.7 | 51.6 | 33.0 | 3.0 |

$F_3$ seeds from the $F_2$ parent plant AX4416-7-2 were planted at Ames, Iowa. Ten individual $F_3$ plants were harvested from the $F_3$ parent plants. The fatty acid composition of the $F_3$ plant AX4416-7-2-2 was determined and is set forth below in Table X:

TABLE X

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4416-7-2-2 | 10.4 | 5.0 | 28.9 | 52.5 | 3.2 |
| FA26591EMS | 9.9 | 7.2 | 25.0 | 49.3 | 8.6 |
| A5 | 9.4 | 4.6 | 28.3 | 52.3 | 5.4 |

$F_4$ seeds from the $F_3$ parent plant AX4416-7-2-2 were planted at Ames, Iowa. Ten individual $F_4$ plants were harvested from the $F_3$ parent plants. The fatty acid composition of the $F_4$ generation was determined and is set forth in Table XI:

TABLE XI

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4416-7-2-2 | 10.1 | 4.9 | 56.4 | 26.9 | 1.7 |
| FA26591EMS | 10.7 | 6.3 | 36.9 | 42.4 | 3.7 |
| A5 | 11.6 | 4.5 | 22.4 | 58.0 | 3.6 |

EXAMPLE 10

This Example describes the crossing of line C1640 with the mutant line FA26591EMS, one of the parents used in Example 9. The hybrid $F_1$ seeds obtained from the cross were designated AX4417.

$F_1$ plants of the cross AX4417 were grown in the Iowa State University—University of Puerto Rico nursery at Isabela, Puerto Rico. $F_2$ seeds were obtained by natural self-pollination. Each $F_1$ plant was harvested individually, and the $F_2$ seeds of each were maintained as separate subpopulations of the cross.

A total of 200 $F_2$ seeds from the cross were planted in the Iowa State University—University of Puerto Rico nursery at Isabela, Puerto Rico. $F_3$ seeds were obtained by natural self-pollination. One hundred $F_2$ plants were harvested individually.

A 10-seed sample from each $F_2$ plant was analyzed by gas-liquid chromatography at Iowa State University. The $F_2$ plant designated AX4417-2-16 was selected with a linolenic acid percentage lower than that of either parent.

The fatty acid composition of the soybeans of the present invention as well as that of the parent mutant lines is set forth in Table XII:

TABLE XII

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4417-2-16 | 10.7 | 4.2 | 49.5 | 33.2 | 2.3 |
| FA26591EMS | 10.0 | 4.2 | 41.4 | 44.3 | 4.5 |
| C1640 | 10.8 | 3.8 | 24.8 | 56.6 | 4.0 |

$F_3$ seeds from the $F_2$ parent plant AX441-2-16 were planted at Ames, Iowa. Ten individual $F_3$ plants were harvested from the $F_2$ parent plants. The fatty acid composition of the $F_3$ plant AX4417-2-16-5 was determined and is set forth below in Table XIII:

TABLE XIII

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4417-2-16-5 | 9.9 | 5.4 | 24.1 | 57.2 | 3.5 |
| FA26591EMS | 9.5 | 6.3 | 26.7 | 49.3 | 8.1 |
| C1640 | 9.3 | 4.0 | 21.3 | 60.5 | 4.9 |

$F_4$ seeds from the $F_3$ parent plant AX4417-2-16-5 were planted at Ames, Iowa. Ten individual $F_4$ plants were harvested from the $F_3$ parent plants. The fatty acid composition of the $F_4$ generation was determined and is set forth in Table XIV:

TABLE XIV

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4417-2-16-5 | 11.6 | 5.6 | 31.6 | 48.9 | 2.4 |
| FA26591EMS | 10.9 | 7.6 | 29.5 | 47.3 | 4.7 |
| C1640 | 10.5 | 4.2 | 23.6 | 57.9 | 3.8 |

EXAMPLE 11

This Example describes the crossing of the mutant line A1937EMS-65 prepared as described in Example 5 with the parent line FA47451EMS, one of the parent lines used in the cross prepared in Example 7. The hybrid $F_1$ seeds obtained from the cross were designated AX4889.

$F_1$ plants from the cross AX4889 were grown in the Iowa State University—University of Puerto Rico nursery at Isabela, Puerto Rico. $F_2$ seeds were obtained by natural self-pollination. Each $F_1$ plant was harvested individually, and the $F_2$ seeds of each were maintained as separate subpopulations of the cross.

$F_2$ seeds from each of these $F_1$ plants designated AX4889-1, AX4889-2 and AX4889-3 were planted in the Iowa State University—University of Puerto Rico nursery at Isabela, Puerto Rico. Seven $F_2$ plants were harvested individually from each of the three subpopulations.

A 10-seed sample from each $F_2$ plant was analyzed by gas-liquid chromatography at Iowa State University. $F_2$ plants designated AX4889-2-6 and AX4889-3-1 were selected as having a linolenic acid content lower than that of either parent.

The fatty acid composition of the soybeans of the present invention as well as that of the parent mutant lines is set forth in Table XV:

TABLE XV

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4889-2-6 | 14.4 | 4.2 | 28.4 | 50.6 | 2.4 |
| AX4889-3-1 | 12.4 | 4.2 | 19.8 | 61.1 | 2.5 |
| FA47451EMS | 16.4 | 4.1 | 23.3 | 51.2 | 4.9 |
| A1937EMS-65 | 12.4 | 4.1 | 21.6 | 57.8 | 4.1 |

EXAMPLE 12

This Example describes the crossing of one of the parent lines used in Example 9 (i.e.—FA26591EMS) with progeny from the cross obtained in Example 6 (the progeny being designated as AX4170-1-1). The hybrid $F_1$ seeds obtained from the crosses were designated AX4561-AX4570.

$F_1$ plants of AX4561-AX4570 were grown in the Iowa State University—University of Puerto Rico nursery at Isabela, Puerto Rico. $F_2$ seeds were Obtained by natural self-pollination. Each $F_1$ plant was harvested individually, and the $F_2$ seeds of each were maintained as separate subpopulations.

A total of 210 $F_2$ seeds from the populations AX4561-AX4570 were planted in the Iowa State University—University of Puerto Rico nursery at Isabela, Puerto Rico. $F_3$ seeds were obtained by natural self-pollination. Approximately 150 $F_2$ plants were harvested individually.

A 5-seed sample from each $F_2$ plant was analyzed by gas-liquid chromatography at Iowa State University. Two $F_2$ plants designated AX4561-2-6 and AX4568-1-7 were selected with a linolenic acid content being lower than that of either parent.

The fatty acid composition of the soybeans of the present invention as well as that of the parent mutant lines is set forth in Table XVI:

TABLE XVI

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4561-2-6 | 8.8 | 3.8 | 59.2 | 26.4 | 1.7 |
| AX4568-1-7 | 11.2 | 3.8 | 59.2 | 25.0 | 1.7 |
| AX4170-1-1 | 16.5 | 4.9 | 28.5 | 47.9 | 2.2 |
| FA26591EMS | 8.6 | 4.9 | 48.4 | 35.0 | 3.1 |

$F_3$ seeds from the $F_2$ plants AX4561-2-6 and AX4568-1-7 were grown in Puerto Rico. Individual $F_3$ plants were harvested. The fatty acid composition of the $F_3$ plants AX4561-2-6-1 and AX4568-1-7-5 was determined and is set forth in Table XVII:

TABLE XVII

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4561-2-6-1 | 9.2 | 3.4 | 65.0 | 21.1 | 1.3 |
| AX4568-1-7-5 | 12.3 | 4.2 | 59.3 | 22.8 | 1.4 |
| AX4170-1-1 | 15.3 | 3.7 | 37.9 | 41.3 | 1.8 |
| FA26591EMS | 9.1 | 4.3 | 58.2 | 25.5 | 2.9 |

$F_4$ seeds from the individual $F_3$ parent plants were planted at the Agricultural Engineering and Agronomy Research Center at Ames, Iowa. Individual plants were harvested from each $F_3$ parent plant. The fatty acid composition of the $F_4$ generation was determined and is set forth in Table XVIII:

TABLE XVIII

| Seed Identification | Fatty Acid Composition | | | | |
|---|---|---|---|---|---|
| | Palmitic Acid (16:0) | Stearic Acid (18:0) | Oleic Acid (18.1) | Linoleic Acid (18:2) | Linolenic Acid (18:3) |
| AX4561-2-6-1 | 9.3 | 5.2 | 50.2 | 33.4 | 1.8 |
| AX4568-1-7-5 | 12.1 | 5.8 | 33.2 | 46.9 | 1.9 |
| AX4170-1-1 | 15.2 | 4.8 | 37.8 | 40.3 | 2.0 |
| FA26591EMS | 10.0 | 4.3 | 44.2 | 38.0 | 3.4 |

EXAMPLE 13

This Example describes the crossing of parent FA26591EMS used in Example 9 and progeny from the soybeans obtained in Example 7 (the progeny being designated AX4172-1-24-2). The hybrid $F_1$ seeds obtained from the cross were designated AX4571.

$F_1$ plants of AX4571 were grown in the Iowa State University—University of Puerto Rico nursery at Isabela, Puerto Rico. $F_2$ seeds were obtained by natural self-pollination. Each $F_1$ plant was harvested individually, and the $F_2$ seeds of each were maintained as separate subpopulations.

A total of 30 $F_2$ seeds from the population AX4571 were planted in the Iowa State University—University of Puerto Rico nursery at Isabela, Puerto Rico. $F_3$ seeds were obtained by natural self-pollination. Approximately 20 $F_2$ plants were harvested individually.

A 5-seed sample from each $F_2$ plant was analyzed by gas-liquid chromatography at Iowa State University. One $F_2$ plant designated AX4571-1-2 was selected with a linolenic acid content being lower than that of either parent.

The fatty acid composition of the soybeans of the present invention as well as that of the parent mutant lines is set forth in Table XIX:

TABLE XIX

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4571-1-2 | 8.2 | 5.0 | 59.6 | 24.9 | 2.3 |
| AX4172-1-24-2 | 10.5 | 4.4 | 38.2 | 42.8 | 4.1 |
| FA26591EMS | 8.6 | 4.9 | 48.4 | 35.0 | 3.1 |

$F_3$ seeds from the $F_2$ plant AX4571-1-2 was grown in Puerto Rico. Individual $F_3$ plants were harvested. The fatty acid composition of the $F_3$ plant AX4571-1-2-1 was determined and is set forth in Table XX:

TABLE XX

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4571-1-2-1 | 8.2 | 4.3 | 66.8 | 19.4 | 1.3 |
| AX4172-1-24-2 | 8.8 | 3.2 | 54.2 | 31.4 | 2.8 |
| FA26591EMS | 9.1 | 4.3 | 58.2 | 25.5 | 2.9 |

$F_4$ seeds from the individual $F_3$ parent plants were planted at the Agricultural Engineering and Agronomy Research Center at Ames, Iowa. Individual plants were harvested from each $F_3$ parent plant. The fatty acid composition of the $F_4$ generation was determined and is set forth in Table XXI:

TABLE XXI

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4571-1-2-1 | 8.9 | 6.1 | 45.5 | 37.4 | 2.1 |
| AX4172-1-24-2 | 9.1 | 5.9 | 40.6 | 41.5 | 2.9 |
| FA26591EMS | 10.0 | 4.3 | 44.2 | 38.0 | 3.4 |

EXAMPLE 14

This Example describes the crossing of the parent FA26591EMS with progeny obtained from the cross described in Example 8 (the progeny being designated as AX4174-1-8-9). The hybrid $F_1$ seeds obtained from the crosses were designated AX4572-AX4588.

$F_1$ plants of AX4572-AX4588 were grown in the Iowa State University—University of Puerto Rico nursery at Isabela, Puerto Rico. $F_2$ seeds were obtained by natural self-pollination. Each $F_1$ plant was harvested individually, and the $F_2$ seeds of each were maintained as separate subpopulations.

A total of 270 $F_2$ seeds from the populations AX4572-AX4588 were planted in the Iowa State University—University of Puerto Rico nursery at Isabela, Puerto Rico. $F_3$ seeds were obtained by natural self-pollination. Approximately 180 $F_2$ plants were harvested individually.

A 5-seed sample from each $F_2$ plant was analyzed by gas-liquid chromatography at Iowa State University. Two $F_2$ plants designated AX4585-1-5 and AX4586-1-2 were selected with a linolenic acid content being lower than that of either parent.

The fatty acid composition of the soybeans of the present invention as well as that of the parent mutant lines is set forth in Table XXII:

TABLE XXII

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4585-1-5 | 9.0 | 3.6 | 50.1 | 35.0 | 2.2 |
| AX4586-1-2 | 9.1 | 4.1 | 55.9 | 28.9 | 2.0 |
| AX4174-1-8-9 | 16.1 | 3.1 | 40.7 | 36.9 | 3.2 |
| FA26591EMS | 8.6 | 4.9 | 48.4 | 35.0 | 3.1 |

$F_3$ seeds from the $F_2$ plants AX4585-1-5 and AX4586-1-2 were grown in Puerto Rico. Individual $F_3$ plants were harvested. The fatty acid composition of the $F_3$ plants AX4585-1-5-3 and AX4586-1-2-1 was determined and is set forth in Table XXIII:

TABLE XXIII

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4585-1-5-3 | 8.4 | 3.3 | 68.0 | 18.9 | 1.3 |
| AX4586-1-2-1 | 8.3 | 3.5 | 70.7 | 16.2 | 1.4 |
| AX4174-1-8-9 | 13.9 | 2.7 | 62.2 | 18.9 | 2.3 |
| FA26591EMS | 9.1 | 4.3 | 58.2 | 25.5 | 2.9 |

$F_4$ seeds from the individual $F_3$ parent plants were planted at the Agricultural Engineering and Agronomy Research Center at Ames, Iowa. Individual plants were harvested from each $F_3$ parent plant. The fatty acid composition of the $F_4$ generation was determined and is set forth in Table XXIV:

TABLE XXIV

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4585-1-5-3 | 8.8 | 4.0 | 55.8 | 29.4 | 2.0 |
| AX4586-1-2-1 | 9.7 | 4.4 | 50.8 | 33.4 | 1.8 |
| AX4174-1-8-9 | 16.6 | 5.3 | 39.2 | 35.8 | 3.1 |
| FA26591EMS | 10.0 | 4.3 | 44.2 | 38.0 | 3.4 |

EXAMPLE 15

This Example describes the crossing of progeny obtained as described in Example 6 with progeny obtained as described in Example 8 (the progeny being designated as AX4170-1-1 and AX4174-1-8-9, respectively). The hybrid $F_1$ seeds obtained from the crosses were designated AX4605-AX4613.

$F_1$ plants of AX4605-AX4613 were grown in the Iowa State University—University of Puerto Rico nursery at Isabela, Puerto Rico. $F_2$ seeds were obtained by natural self-pollination. Each $F_1$ plant was harvested individually, and the $F_2$ seeds of each were maintained as separate subpopulations.

A total of 210 $F_2$ seeds from the populations AX4605-AX4613 were planted in the Iowa State University—University of Puerto Rico nursery at Isabela, Puerto Rico. $F_3$ seeds were obtained by natural self-pollination. Approximately 170 $F_2$ plants were harvested individually.

A 5-seed sample from each $F_2$ plant was analyzed by gas-liquid chromatography at Iowa State University. Two $F_2$ plants designated AX4611-1-14 and AX4612-1-12 were selected with a linolenic acid content being lower than that of either parent.

The fatty acid composition of the soybeans of the present invention as well as that of the parent mutant lines is set forth in Table XXV:

TABLE XXV

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4611-1-14 | 16.7 | 3.7 | 40.4 | 37.1 | 2.0 |
| AX4612-1-12 | 11.8 | 3.6 | 43.9 | 38.7 | 2.0 |
| AX4170-1-1 | 16.5 | 4.9 | 28.5 | 47.9 | 2.2 |
| AX4174-1-8-9 | 16.1 | 3.1 | 40.7 | 36.9 | 3.2 |

$F_3$ seeds from the $F_2$ plants AX4611-1-14 and AX4612-1-12 were grown in Puerto Rico. Individual $F_3$ plants were harvested. The fatty acid composition of the $F_3$ plants AX4611-1-14-3 and AX4612-1-12-2 was determined and is set forth in Table XXVI:

TABLE XXVI

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4611-1-14-3 | 13.7 | 2.8 | 59.0 | 23.0 | 1.4 |
| AX4612-1-12-2 | 12.2 | 2.5 | 64.6 | 20.0 | 1.4 |
| AX4170-1-1 | 15.3 | 3.7 | 37.9 | 41.3 | 1.8 |
| AX4174-1-8-9 | 13.9 | 2.7 | 62.2 | 18.9 | 2.3 |

$F_4$ seeds from the individual $F_3$ parent plants were planted at the Agricultural Engineering and Agronomy Research Center at Ames, Iowa. Individual plants were harvested from each $F_3$ parent plant. The fatty acid composition of the $F_4$ generation was determined and is set forth in Table XXVII:

TABLE XXVII

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4611-1-14-3 | 16.1 | 5.4 | 34.4 | 42.2 | 1.9 |
| AX4612-1-12-2 | 14.6 | 5.0 | 38.4 | 40.1 | 1.9 |
| AX4170-1-1 | 15.2 | 4.8 | 37.8 | 40.3 | 2.0 |
| AX4174-1-8-9 | 16.6 | 5.3 | 39.2 | 35.8 | 3.1 |

EXAMPLE 16

This Example describes the crossing of the progeny obtained from Example 7 (designated as AX4172-1-24-2) with progeny obtained as described in Example 8 (designated as AX4174-1-2-3) to obtain soybean lines in accordance with the present invention. The hybrid $F_1$ seeds obtained from the cross were designated as AX4591-AX4604.

$F_1$ plants of AX4591-AX4604 were grown in the Iowa State University—University of Puerto Rico nursery at Isabela, Puerto Rico. $F_2$ seeds were obtained by natural self-pollination. Each $F_1$ plant was harvested individually, and the $F_2$ seeds of each were maintained as separate subpopulations.

A total of 500 $F_2$ seeds from the populations AX4591-AX4604 were planted in the Iowa State University—University of Puerto Rico nursery at Isabela, Puerto Rico. $F_3$ seeds were obtained by natural self-pollination. Approximately 425 $F_2$ plants were harvested individually.

A 5-seed sample from each $F_2$ plant was analyzed by gas-liquid chromatography at Iowa State University. Two $F_2$ plants designated AX4592-1-28 and AX4597-1-36 were selected with a linolenic acid content being lower than that of either parent.

The fatty acid composition of the soybeans of the present invention as well as that of the parent mutant lines is set forth in Table XXVIII:

TABLE XXVIII

| | Fatty Acid Composition | | | | |
|---|---|---|---|---|---|
| Seed Identification | Palmitic Acid (16:0) | Stearic Acid (18:0) | Oleic Acid (18:1) | Linoleic Acid (18:2) | Linolenic Acid (18:3) |
| AX4592-1-28 | 10.6 | 4.0 | 54.4 | 28.4 | 2.7 |
| AX4597-1-36 | 9.3 | 3.4 | 61.4 | 23.5 | 2.3 |
| AX4172-1-24-2 | 10.5 | 4.4 | 38.2 | 42.8 | 4.1 |
| AX4174-1-2-3 | 16.6 | 3.6 | 29.4 | 47.1 | 3.3 |

$F_3$ seeds from the $F_2$ plants AX4592-1-28 and AX4597-1-36 were grown in Puerto Rico. Individual $F_3$ plants were harvested. The fatty acid composition of the $F_3$ plants AX4592-1-28-2 and AX4597-1-36-3 was determined and is set forth in Table XXIX:

TABLE XXIX

| | Fatty Acid Composition | | | | |
|---|---|---|---|---|---|
| Seed Identification | Palmitic Acid (16:0) | Stearic Acid (18:0) | Oleic Acid (18:1) | Linoleic Acid (18:2) | Linolenic Acid (18:3) |
| AX4592-1-28-2 | 8.8 | 3.4 | 70.3 | 15.9 | 1.7 |
| AX4597-1-36-3 | 7.7 | 3.2 | 71.2 | 15.9 | 2.1 |
| AX4172-1-24-2 | 8.8 | 3.2 | 54.2 | 31.4 | 2.3 |
| AX4174-1-2-3 | 15.1 | 2.9 | 45.8 | 33.7 | 2.6 |

$F_4$ seeds from the individual $F_3$ parent plants were planted at the Agricultural Engineering and Agronomy Research Center at Ames, Iowa. Individual plants were harvested from each $F_3$ parent plant. The fatty acid composition of the $F_4$ generation was determined and is set forth in Table XXX:

TABLE XXX

| | Fatty Acid Composition | | | | |
|---|---|---|---|---|---|
| Seed Identification | Palmitic Acid (16:0) | Stearic Acid (18:0) | Oleic Acid (18:1) | Linoleic Acid (18:2) | Linolenic Acid (18:3) |
| AX4592-1-28-2 | 9.1 | 5.4 | 43.8 | 39.3 | 2.5 |
| AX4597-1-36-3 | 9.0 | 4.6 | 48.4 | 35.6 | 2.4 |
| AX4172-1-24-2 | 9.1 | 5.9 | 40.6 | 41.5 | 2.9 |
| AX4174-1-2-3 | 15.1 | 4.1 | 43.6 | 34.4 | 2.9 |

EXAMPLE 17

This Example reflects the heritability of the low linolenic acid trait in the lines A16 and A17, viz.—progeny produced from the cross described in Example 6.

A16 and A17 seeds were allowed to self-pollinate and were also crossed with the following parents: Century 84 (a commercial cultivar), C1640 and their parents (viz.—A5 and FA47437EMS). These were planted in Ames, Iowa, in 1988.

The mean linolenic acid percentage of the self-pollinated seeds and the hybrid seeds from crosses between A16 and the four other genotypes were obtained and are summarized in Table XXXI:

TABLE XXXI

| | Parent Mated With A16 | | | |
|---|---|---|---|---|
| Entry | Century 84 | C1640 | A5 | FA47437EMS |
| Parent Mean Linolenic Acid Content | | | | |
| A16 | 2.1* | 1.9* | 2.3* | 1.7* |
| Other Parent | 7.6 | 3.2 | 2.9 | 3.7 |
| Hybrid Seed Mean Linolenic Acid Content | | | | |
| One Cross | 3.7* | 2.4* | 2.5 ns | 2.6 ns |
| Reciprocal Cross | 5.2 | 3.0 | 2.4 | 2.9 |
| (0.05 - Least Significant Difference) | 0.45 | 0.25 | 0.19 | 0.44 |

*Selfed seed of the two parents or hybrid seed from the reciprocal crosses were significantly different at the 0.05 probability level.
ns Hybrid seeds from reciprocal crosses were not significantly different.

The mean linolenic acid percentage of the self-pollinated seeds and the hybrid seeds from crosses between A17 and the other four genotypes were obtained and are summarized in Table XXXII:

TABLE XXXII

| | Parent Mated With A17 | | | |
|---|---|---|---|---|
| Entry | Century 84 | C1640 | A5 | FA47437EMS |
| Parent Mean Linolenic Acid Content | | | | |
| A17 | 2.2* | 2.1* | 1.6* | 1.8* |
| Other Parent | 8.3 | 3.6 | 2.6 | 4.7 |
| Hybrid Seed Mean Linolenic Acid Content | | | | |
| One Cross | 3.7* | 2.3* | 2.2 ns | 3.2 ns |
| Reciprocal Cross | 5.1 | 3.0 | 2.2 | 3.0 |
| (0.05 - Least Significant Difference) | 0.79 | 0.12 | 0.22 | 0.70 |

*Selfed seed of the two parents or hybrid seed from the reciprocal crosses were significantly different at the 0.05 probability level.
ns Hybrid seeds from reciprocal crosses were not significantly different.

The Tables XXXI and XXXII support the conclusion that there is a partial maternal effect expressed when A16 and A17 are crossed with Century 84 and C1640 but not when these soybean lines are crossed with their parents. The partial maternal effect means that the genotype of the plant has a partial influence on the linolenic acid percentage of the seed produced on it, and the genotype of the seed also has a partial influence on its linolenic acid percentage. The absence of a maternal effect would indicate that the genotype of the seed entirely controls its linolenic acid percentage.

With either partial or no maternal inheritance, it is possible to select among $F_2$ seeds on $F_1$ plants for linolenic acid percentage. This speeds up the transfer of genes from one parent to another by carrying out backcrossing techniques.

The analyses of individual $F_2$ seed from the crosses A16 with Century 84 and A17 with Century 84 were conducted with seeds harvested in January, 1989, in Puerto Rico. The mean linolenic acid content was 1.9% for A16, 2.1% for A17, and 8.3% for Century 84. Seven out of 154 (4.5%) of the $F_2$ seeds had a linolenic acid content of less than 2.5%. Based upon this data, it can be concluded that the low linolenic acid is an inherited trait, the low percentage obtained indicates that multiple genes control the trait and that, in a backcrossing program, selection should be practiced among $F_2$ seeds or plants; and plants grown from those with low linolenic acid should be backcrossed to the recurrent parent.

Backcrossing can be used successfully to transfer the low linolenic acid genes from A16 and A17 to high-yielding cultivars like Century 84. The percentage of $F_2$ seeds in each backcross generation with less than 2.5% linolenic acid has been about 4%. This is an adequate percentage of useful segregates to use in a backcrossing program.

EXAMPLE 18

This Example determines the fatty acid composition of five soybean genotypes to evaluate the effect of varied planting dates.

As previously indicated, A16 is the same as AX4170-1-1-2; and A17 is the same as AX4170-1-15-2. The soybean variety C1640 is a moderately low linolenic acid genotype developed by USDA/Purdue and is publicly available. C1640 was used as a control line along with the commercial soybean cultivar, Century, from which C1640 was obtained by chemical mutagenesis.

The fatty acid composition of the seed oil of five soybean genotypes is illustrated in Table XXXIII. The five varieties were planted in the field on May 1, May 15, May 30 and June 15 at Iowa State University, Ames, Iowa. Three replications of a randomized complete block design for each variety were used with a split-plot arrangement of genotypes as whole plots and planting dates as subplots.

TABLE XXXIII

| Planting Date Genotype | Fatty Acid Percentages | | | | |
|---|---|---|---|---|---|
| | Palmitic | Stearic | Oleic | Linoleic | Linolenic |
| May 1 | | | | | |
| A16 | 11.2 | 6.4 | 37.6 | 42.2 | 1.9 |
| A17 | 15.3 | 5.5 | 35.4 | 41.0 | 2.0 |
| A5 | 9.8 | 5.5 | 47.7 | 33.6 | 2.8 |
| C1640 | 11.3 | 4.3 | 25.4 | 55.2 | 3.4 |
| Century | 11.1 | 4.3 | 22.6 | 54.9 | 6.7 |
| May 15 | | | | | |
| A16 | 11.8 | 6.2 | 35.0 | 44.3 | 2.1 |
| A17 | 15.5 | 5.5 | 34.3 | 41.7 | 2.0 |
| A5 | 9.9 | 5.4 | 50.1 | 31.4 | 2.6 |

TABLE XXXIII-continued

| Planting Date Genotype | Fatty Acid Percentages | | | | |
|---|---|---|---|---|---|
| | Palmitic | Stearic | Oleic | Linoleic | Linolenic |
| C1640 | 11.6 | 4.3 | 25.2 | 55.4 | 3.4 |
| Century | 11.4 | 4.1 | 24.6 | 53.4 | 6.3 |
| May 30 | | | | | |
| A16 | 12.0 | 5.9 | 31.8 | 47.6 | 2.2 |
| A17 | 16.6 | 5.1 | 30.9 | 44.0 | 2.4 |
| A5 | 10.8 | 5.6 | 45.7 | 34.3 | 3.0 |
| C1640 | 11.1 | 4.5 | 24.9 | 55.2 | 4.0 |
| Century | 10.9 | 4.4 | 25.7 | 52.4 | 6.4 |
| June 15 | | | | | |
| A16 | 12.1 | 6.0 | 27.9 | 51.1 | 2.4 |
| A17 | 16.6 | 4.7 | 29.2 | 46.2 | 2.3 |
| A5 | 11.2 | 5.0 | 37.0 | 43.2 | 3.1 |
| C1640 | 10.4 | 5.2 | 23.2 | 57.0 | 3.9 |
| Century | 10.3 | 5.1 | 23.4 | 54.3 | 6.5 |
| LSD (0.05) | 0.38 | 0.38 | 3.54 | 3.27 | 0.49 |

These results indicate that A16 and A17 reproducibly exhibit the low linolenic acid phenotype. The later in the season the soybeans were planted, the higher the linolenic acid concentration. For example, the A16 planted on May 1 at Ames, Iowa, had 1.9% linolenic acid; the May 15 planting had 2.1% linolenic acid; the May 30 planting had 2.2% linolenic acid; and the June 15 planting had 2.4% linolenic acid. The earlier in the season the planting is made, the lower the linolenic acid level exhibited. However, in all four plantings, the level exhibited was less than 2.5% linolenic acid and was significantly less than the linolenic acid content of A5.

The development and maturation under high temperature conditions of the soybeans of the present invention results in lower levels of linolenic acid, as illustrated in Table XXXIII. Table XXXIV illustrates the temperature and day length data corresponding to five soybean genotypes described in Table XXXIII. The temperature and day length data for A16, A17, A5, C1640 and Century were recorded for plantings in the field on May 1, May 15, May 30 and June 15 at Iowa State University in Ames, Iowa. R1 is the stage of plant development when there is one open flower at any node on the main stem. R5 is when there is a seed 3 mm long in a pod at one of the four uppermost nodes on the main stem with a fully developed leaf. R7 is when there is one normal pod on the main stem that has reached its mature pod color. The final development and maturation during the hotter summer months resulted in the lowest levels of linolenic acid detected among the four plantings (Table XXXIII).

TABLE XXXIV

| Planting Date Genotype | Reproductive Stages | | | R1 to R7 | | | R5 to R7 | | |
|---|---|---|---|---|---|---|---|---|---|
| | R1 (mo-day) | R5 (mo-day) | R7 (mo-day) | No. of Days | Avg. Daily High Temp. (F°) | Avg. Day Length (hr-min) | No. of Days | Avg. Daily High Temp. (F°) | Avg. Day Length (hr-min) |
| May 1 | | | | | | | | | |
| A16 | 6-21 | 7-21 | 8-18 | 59 | 91 | 14-43 | 29 | 92 | 14-19 |
| A17 | 6-19 | 7-14 | 8-13 | 56 | 91 | 14-40 | 31 | 98 | 14-31 |
| A5 | 6-20 | 7-15 | 8-11 | 53 | 90 | 14-50 | 28 | 90 | 14-32 |
| C1640 | 6-20 | 7-25 | 8-29 | 71 | 90 | 14-32 | 36 | 90 | 14-01 |
| Century | 6-21 | 7-17 | 8-31 | 72 | 90 | 14-29 | 46 | 89 | 14-07 |
| May 15 | | | | | | | | | |
| A16 | 6-29 | 7-21 | 8-21 | 54 | 90 | 14-34 | 32 | 92 | 14-15 |
| A17 | 6-24 | 7-17 | 8-16 | 54 | 91 | 14-43 | 31 | 90 | 14-25 |
| A5 | 6-24 | 7-17 | 8-16 | 54 | 91 | 14-43 | 31 | 90 | 14-25 |
| C1640 | 6-28 | 7-30 | 9-02 | 67 | 89 | 14-22 | 35 | 90 | 13-50 |
| Century | 6-25 | 7-24 | 8-31 | 68 | 89 | 14-26 | 39 | 90 | 14-00 |
| May 30 | | | | | | | | | |
| A16 | 7-14 | 7-30 | 8-30 | 48 | 89 | 14-11 | 32 | 90 | 13-54 |
| A17 | 7-10 | 7-26 | 8-23 | 45 | 91 | 14-23 | 29 | 93 | 14-07 |
| A5 | 7-09 | 7-26 | 8-23 | 46 | 91 | 14-24 | 29 | 93 | 14-07 |
| C1640 | 7-09 | 8-06 | 9-07 | 61 | 88 | 17-07 | 33 | 87 | 13-35 |
| Century | 7-09 | 7-30 | 9-08 | 62 | 88 | 14-05 | 41 | 88 | 13-43 |
| June 15 | | | | | | | | | |
| A16 | 7-24 | 8-09 | 9-07 | 46 | 88 | 13-51 | 30 | 86 | 13-32 |
| A17 | 7-20 | 8-01 | 9-04 | 47 | 88 | 13-59 | 35 | 89 | 13-45 |
| A5 | 7-20 | 8-07 | 9-05 | 48 | 88 | 13-58 | 30 | 88 | 13-37 |
| C1640 | 7-21 | 8-13 | 9-22 | 64 | 86 | 13-35 | 41 | 84 | 13-06 |
| Century | 7-22 | 8-10 | 9-18 | 59 | 87 | 13-39 | 40 | 85 | 13-16 |

EXAMPLE 19

This Example describes the crossing of parent lines A17 with A6 to obtain soybean lines of the present invention characterized by high stearic acid and low linolenic acid contents. The hybrid $F_1$ seeds were designated AX5082-AX5083.

$F_1$ plants were grown as described in Example 6. $F_1$ plants of AX5082-AX5083 were grown in the Iowa State University—University of Puerto Rico nursery at Isabela, Puerto Rico. $F_2$ seeds were obtained by natural self-pollination. There were 21 $F_2$ plants harvested individually from each of the populations AX5082 and AX5083.

Individual $F_3$ seeds from $F_2$ plants were analyzed by gas-liquid chromatography at Iowa State University for fatty acid composition. Table XXXV sets forth the fatty acid composition of soybeans according to the present invention characterized by a high stearic acid and low linolenic acid content as well as that of the parent lines:

TABLE XXXV

| | Fatty Acid Composition | | | | |
|---|---|---|---|---|---|
| Seed Identification | Palmitic Acid (16:0) | Stearic Acid (18:0) | Oleic Acid (18:1) | Linoleic Acid (18:2) | Linolenic Acid (18:3) |
| AX5083-2-2-7 | 6.9 | 32.0 | 38.3 | 20.5 | 2.3 |
| AX5083-3-6-1 | 6.8 | 28.2 | 35.0 | 28.3 | 1.8 |
| AX5083-3-6-5 | 7.8 | 29.7 | 32.0 | 28.8 | 1.7 |
| AX5083-3-6-10 | 8.0 | 23.0 | 24.7 | 42.4 | 2.0 |
| A17 | 15.1 | 3.3 | 40.4 | 39.0 | 2.1 |
| A6 | 7.3 | 25.2 | 26.4 | 35.6 | 5.4 |

EXAMPLE 20

This Example describes the crossing of AX4170-1-1-3 and AX4174-1-8-9 to obtain the soybean line of the present invention characterized by high oleic acid content.

The parent line AX4170-1-1-3 was prepared in a manner similar to that for AX4170-1-1-2 as described in Example 6. Then, $F_4$ seeds from $F_3$ parent plant AX4170-1-1-3 were planted at the Agricultural Engineering and Agronomy Research Center. Individual $F_4$ plants were used for crossing. The parent line AX4174-1-8-9 is the line also used in Examples 14 and 15.

Crosses were made between individual plants of AX4170-1-1-3 and AX4174-1-8-9 at the Agricultural Engineering and Agronomy Research Center during the summer. The hybrid $F_1$ seeds obtained from the cross were designated AX4612.

$F_1$ seed was planted in the Iowa State University—University of Puerto Rico nursery at Isabela, Puerto Rico, in October. $F_2$ seeds were obtained by natural self-pollination of the $F_1$ plants. Each $F_1$ plant was harvested individually. The $F_2$ seeds of each plant were maintained as a separate subpopulation.

Thirty $F_2$ seeds from each of the $F_1$ plants, designated AX4612-1 and AX4612-2, and seeds of the parents were planted in Puerto Rico in February. Fourteen $F_2$ plants from AX4612-1 and 11 $F_2$ plants from AX4612-2 were harvested individually. A 5-seed sample from each $F_2$ plant and from plants of the parents were analyzed for fatty acid composition by gas-liquid chromatography.

Table XXXVI summarizes the analysis of the fatty acid composition of the $F_3$ seed from the $F_2$ plant, obtained in Puerto Rico, having the desired high oleic acid content and seed from that of the parent lines:

TABLE XXXVI

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4612-1-13 | 12.5 | 4.4 | 56.6 | 24.4 | 2.0 |
| AX4170-1-1-3 | 16.4 | 5.2 | 24.5 | 51.4 | 2.6 |
| AX4174-1-8-9 | 15.1 | 3.3 | 44.4 | 34.4 | 2.9 |

Table XXXVII summarizes the analysis of the fatty acid composition of the $F_4$ seed obtained from the $F_3$ progeny from the $F_2$ plant AX4612-1-13 having the desired high oleic acid content, as well as seed from that of the parents as obtained from a planting in Puerto Rico in August:

TABLE XXXVII

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX4612-1-13-3 | 10.5 | 3.8 | 64.3 | 20.2 | 1.3 |
| AX4170-1-1-3 | 15.3 | 3.7 | 37.9 | 41.3 | 1.8 |
| AX4174-1-8-9 | 14.6 | 2.9 | 58.4 | 21.7 | 2.4 |

EXAMPLE 21

This Example describes the crossing of AX4585-1-5-3 with AX5152-7 to obtain the soybean line of the present invention characterized by high oleic, low palmitic, low stearic, and low linolenic acids.

The description of line C1726, the preparation of mutant line A1937NMU-173, and the crossing of C1726 with A1937NMU-173 to obtain line AX5152-7 are described in our copending application, Ser. No. 461,361. The disclosure of that copending application as regards these aspects is herein incorporated by reference. The parent line AX4585-1-5-3 is the line also used in Example 14.

Crosses were made between individual plants of AX4585-1-5-3 and AX5152-7 at the Agricultural Engineering and Agronomy Research center during the summer. The hybrid $F_1$ seeds obtained from the crosses were designated AX6043.

$F_1$ seed was planted in the Iowa State University—University of Puerto Rico nursery at Isabela, Puerto Rico, in October. $F_2$ seeds were obtained by natural self-pollination of the $F_1$ plants. Each $F_1$ plant was harvested individually. The $F_2$ seeds of each $F_1$ plant were maintained as a separate subpopulation.

Twelve $F_2$ seeds from each of the $F_1$ plants, designated AX6043-1 through AX6043-5 and seeds of the parents were planted in Puerto Rico in February, 1990. Six $F_2$ plants were harvested individually from each subpopulation. A 5-seed sample from each $F_2$ and parent plant was analyzed for fatty acid composition by gas-liquid chromatography.

Table XXXVIII summarizes the analysis of the fatty acid composition of the $F_3$ seed from the $F_2$ plant, AX6043-5-3, obtained in Puerto Rico, having the desired composition and seed from that of the parent lines:

TABLE XXXVIII

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX6043-5-3 | 5.1 | 2.8 | 66.4 | 23.6 | 2.0 |
| AX4585-1-5-3 | 8.4 | 4.5 | 62.6 | 22.8 | 1.7 |
| AX5152-7 | 3.8 | 3.8 | 23.5 | 61.4 | 7.6 |

EXAMPLE 22

This Example describes the backcrossing of A89-269077, a 2.0% linolenic cultivar, with AX7345-2, an $F_1$ plant of the cross AX5152-115 with A89-269077, to obtain the soybean line of the present invention characterized by low linolenic and low palmitic acid contents.

Backcrossing was carried out in 1990 at the Agricultural Engineering and Agronomy Research Center. The hybrid $BC_1F_1$ seeds obtained from the cross were designated AX7777.

$BC_1F_1$ seeds of the cross AX7777 were planted in November in the Iowa State University—University of Puerto Rico nursery at Isabela, Puerto Rico. $BC_1F_2$ seeds were obtained by natural self-pollination. A total of 927 $BC_1F_2$ seeds from the cross were planted in Puerto Rico in February. $BC_1F_3$ seeds were obtained by natural self-pollination. Three seeds were harvested from each $BC_1F_2$ plant to obtain a bulk sample of $BC_1F_3$ seeds from the population. A random sample of 480 $BC_1F_3$ seeds was planted at the Agricultural Engineering and Agronomy Research Center near Ames, Iowa, in May. Approximately 334 $BC_1F_3$ plants were harvested individually, and a 10-seed sample from each plant was analyzed by gas-liquid chromatography to determine fatty acid composition.

Table XXXIX sets forth the fatty acid composition of the $BC_1F_3$ plant characterized by a low palmitic acid and low linolenic acid content, as well as that of the parent lines:

TABLE XXXIX

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX7777-7-30 | 3.9 | 3.5 | 38.3 | 52.2 | 2.1 |
| A89-269077 | 10.0 | 4.4 | 37.5 | 46.2 | 2.0 |
| AX5152-115 | 3.6 | 4.0 | 33.4 | 53.0 | 6.0 |

EXAMPLE 23

This Example describes the crossing of AX7689-1-75 with A89-269077 to obtain the soybean line of the present invention characterized by low linolenic and high oleic acid contents.

Crosses were made at the Iowa State University—University of Puerto Rico nursery during December 1990. The hybrid $F_1$ seeds obtained from the cross were designated AX8095.

$F_1$ seeds of the cross AX8095 were planted in February in the Iowa State University—University of Puerto Rico nursery at Isabela, Puerto Rico. $F_2$ seeds were obtained by natural self-pollination. Each $F_1$ plant was harvested individually, and the $F_2$ seeds of each were maintained as separate subpopulations.

Ten individual F₂ seeds from each F₁ plant were split so that the embryonic axis was left intact. The portion without the embryonic axis (approximately one-third of the seed) was analyzed for fatty acid composition.

Table XXXX summarizes the analysis of the fatty acid composition of an F₂ seed having the desired high oleic acid and low linolenic acid content and that of the parent lines:

TABLE XXXX

| Seed Identification | Fatty Acid Composition | | | | |
|---|---|---|---|---|---|
| | Palmitic Acid (16:0) | Stearic Acid (18:0) | Oleic Acid (18:1) | Linoleic Acid (18:2) | Linolenic Acid (18:3) |
| AX8095-2 | 8.8 | 3.2 | 72.4 | 14.4 | 1.2 |
| AX7689-1-75 | 8.4 | 3.4 | 57.6 | 28.8 | 1.8 |
| A89-269077 | 9.4 | 3.6 | 54.0 | 31.4 | 1.5 |

The present invention discloses methods for the production of soybeans containing low levels of linolenic acid. Such low levels of linolenic acid make the soybean products, such as soybean oil, more suitable for consumption by reducing or eliminating the presence of undesirable linolenic acid oxidation products which have undesirable flavor properties. In addition, the present invention further provides the ability to obtain soybean lines having various palmitic, stearic, oleic, and linoleic acid contents as may be desired for particular applications. It is within the scope of the present invention to alter, if desired for a particular application, the soybeans of this invention by including other fatty acids, as by genetic alteration or by any other means. Indeed, if useful for a particular application, the soybeans of the present invention may be altered as desired so long as the characteristic low linolenic acid trait and other desired traits are retained.

Although the foregoing invention has been described in detail with examples for purposes of better understanding the invention, it will be understood by those skilled in the art that various modifications of the invention may be practiced while remaining within the spirit and the scope of the appended claims.

What is claimed is:

1. A soybean seed designated A16 having ATCC Accession No. 40538 and its descendents which are capable of yielding an endogenously formed vegetable oil exhibiting a linolenic acid content of less than 2.5% by weight based upon the total fatty acid content.

2. Soybean seeds according to claim 1 that are provided as an assemblage of such seeds.

3. Soybean plant produced by the seed of claim 1.

* * * * *

UNITED STATES PATENT AND TRADEMARK OFFICE
CERTIFICATE OF CORRECTION

PATENT NO. : 5,710,369

DATED : January 20, 1998

INVENTOR(S) : Walter R. Fehr et al.

It is certified that error appears in the above-indentified patent and that said Letters Patent is hereby corrected as shown below:

Title page

At [73] delete "Des Moines" and insert --Ames--.

Signed and Sealed this

Fifth Day of May, 1998

BRUCE LEHMAN

*Attest:*

*Attesting Officer*  *Commissioner of Patents and Trademarks*